(12) United States Patent
Fadel et al.

(10) Patent No.: US 7,585,833 B2
(45) Date of Patent: Sep. 8, 2009

(54) MALODOR COVERING PERFUMERY

(75) Inventors: Addi Fadel, Shelton, CT (US); Richard Turk, Plymouth, MA (US); Grant Mudge, West Redding, CT (US); Dana Sullivan, Carmel, NY (US); Veronica Goberdhan, Fairfield, CT (US); Annette De Meo, Shelton, CT (US)

(73) Assignee: Givaudan Fragrances Corporation, Mount Olive, NJ (US)

( * ) Notice: Subject to any disclaimer, the term of this patent is extended or adjusted under 35 U.S.C. 154(b) by 584 days.

(21) Appl. No.: 11/357,314

(22) Filed: Feb. 17, 2006

(65) Prior Publication Data

US 2006/0207037 A1    Sep. 21, 2006

Related U.S. Application Data

(60) Provisional application No. 60/653,706, filed on Feb. 17, 2005.

(51) Int. Cl.
*A61Q 5/10*   (2006.01)
*A61Q 5/12*   (2006.01)
*A61K 8/06*   (2006.01)
*A61K 8/02*   (2006.01)
*G06F 17/50*  (2006.01)

(52) U.S. Cl. .............................. 512/1; 424/70.6; 8/404; 703/12

(58) Field of Classification Search ................. 424/401, 424/70.1; 512/1; 703/12
See application file for complete search history.

(56) References Cited

U.S. PATENT DOCUMENTS

| | | | | |
|---|---|---|---|---|
| 5,656,280 | A  * | 8/1997 | Herb et al. ................. | 424/401 |
| 6,403,075 | B1   | 6/2002 | Costa ......................... | 424/76.1 |
| 6,741,954 | B2 * | 5/2004 | Sonnenberg et al. ........... | 703/2 |
| 2002/0058017 | A1 * | 5/2002 | Tajima et al. .............. | 424/70.1 |

* cited by examiner

*Primary Examiner*—David R Sample
*Assistant Examiner*—Aaron Greso
(74) *Attorney, Agent, or Firm*—Morgan Lewis & Bockius LLP

(57) ABSTRACT

Methods of formulating products having nitrogen-based components to reduce malodor thereof and formulating fragrances to add to the product include selecting at least one malodor-reducing odorant determined by calculated values of air impact, flux, dipole moment, clogP and hydrogen bond donor and acceptor indexes and adding the fragrance to the product to mask malodor.

13 Claims, 10 Drawing Sheets
(9 of 10 Drawing Sheet(s) Filed in Color)

MALODOR COVERING PERFUMERY

CROSS-REFERENCE TO RELATED APPLICATIONS

Applicants claim priority benefits under 35 U.S.C. §119(e) of U.S. Provisional Patent Application Ser. No. 60/653,706 filed Feb. 17, 2005.

FIELD OF THE INVENTION

The present invention relates to the field of fragrances. More specifically, this invention relates to a fragrances and methods of formulating fragrances and products containing fragrances to mask malodor present in products containing ammonia and substituted amines.

BACKGROUND OF THE INVENTION

Many of commercial, industrial, household, and personal care products are designed to mask malodor in the environment to which they are applied or in which they are used. Products may also generate malodor during and/or upon application or use or may themselves be inherently malodorous due to their constituents and functional raw ingredients.

Malodor inherent to cosmetic, industrial and household formulations is an extensive and ubiquitous problem common to many different applications ranging from household cleaners to personal care products including antiperspirants, deodorants, sunless tanners, hair colorants, shampoos and conditioners, hand and body lotions, hair perming and relaxing agents, and the like.

Permanent hair colorants are some of the most challenging formulations to fragrance since they contain ammonia. Due to ammonia's physical properties, such as very high vapor pressure, and its very pungent and offensive perceived olfactive profile, it is considered one of the most difficult malodors to cover using targeted malodor covering perfumery. Semi-permanent or demi-permanent hair colorants contain various substituted amines, sometimes with ammonia present in addition.

Permanent and demi-permanent hair coloring products contain various degrees of ammonia concentrations along with different types of primary, secondary and tertiary amines. Ammonia is an integral part of permanent hair coloring since its numerous roles include: the swelling and the softening of hair to help individual dyes penetrate the hair cuticle into the cortex; acceleration of the oxidative polymerization of colorants by raising the pH inside the hair; activation of the peroxide to activate bleaching and hence, achieve "lifting" of the existing hair color.

Covering the perception of ammonia in products, such as permanent hair coloring products, remains a formidable task despite numerous attempts at creating ways and methods to do so. The difficulty to cover ammonia lies in the necessity to cover ammonia physically rather than chemically since the creation of any type of chemical bond between ammonia and another odorant or chemicals in the formulation will result in a less performing, and sometime even unstable product.

Cosmetic hair colorants referred to as "level 2" are one way to reduce the consumer's exposure to ammonia and its malodor by introducing substituted amines as alkalizing agents in lieu of ammonia. The substituted amines are sometimes used in combination with lower concentrations of ammonia to help these seemingly less harsh formulations in the lifting of existing hair color. Unfortunately, these products do not achieve the results obtained using a true permanent hair coloring system based on ammonia. Some of the disadvantages of a non permanent hair color formulation are less color lift, less dye take and faster fading of the colorants.

Other systems are available and are marketed as a safer alternative to ammonia hair colorants. Alternative available alternative formulations are based on auto-oxidative dyes. Other marketed safer products are in the form of powdered mixtures made of solid dyes (usually in their sulfated form) along with a solid oxidant (typically sodium perborate) activated by the addition of water. These products often result in very drab colors and give the consumer a limited palette of colors.

There remains a need to provide ammonia malodor masking in products such as permanent hair colorants without losing the benefits of the ammonia component, namely its ability of dye uptake and hair color lifting.

Methods of covering ammonia malodor known in the art have been limited to empirical observations and explanations of narrow physico-chemical mechanisms, whereby fragrance materials are chosen to cover malodor based on their hedonic performance.

For instance, U.S. Pat. No. 6,403,075 addresses fragrance materials with a phenyl ring moiety and air diffusion coefficient larger than 5.7 and/or odorants with C-5 ring moiety with at least $sp^2$ hybridized C that were empirically observed to be good ammonia masking agents. In U.S. Patent Application No. 2002/0058017A1, cis-3-hexenol was determined to empirically mask ammonia well in permanent hair coloring systems based on empirical observations.

SUMMARY OF THE INVENTION

In one aspect of the present invention, a method of formulating a product with reduced nitrogen-based malodor comprising providing a product having a nitrogen-based component and adding to the product a fragrance comprising at least one malodor-reducing odorant having an air impact value and a flux value, the product of the air impact and flux values equaling about $5 \times 10^{-13}$ and greater is provided.

In another aspect of the present invention, a method of formulating a product with reduced nitrogen-based malodor comprising providing a product having a nitrogen-based component and adding to the product a fragrance comprising at least one malodor-reducing odorant having a dipole moment of about 1.7 debye and greater, a clogP value of about 4.0 and greater, and either a hydrogen bond donor or a hydrogen bond acceptor index of about 0.1 and greater, is provided.

In another aspect of the present invention, a method of formulating a fragrance to reduce malodor in a nitrogen-based product comprising calculating air impact and flux values for a group of odorants, selecting at least one malodor-reducing odorant having a product of air impact and a flux value equaling about $5 \times 10^{-13}$ and greater, and adding the odorant to the product is provided.

In another aspect of the present invention, a method of formulating a fragrance to reduce malodor in a nitrogen-based product comprising calculating dipole moment, clogP and hydrogen bond donator and acceptor indexes, selecting at least one malodor-reducing odorant having a dipole moment of about 1.7 debye and greater, a clogP value of about 4.0 and greater, and either a hydrogen bond donor or a hydrogen bond acceptor index of about 0.1 and greater, and adding the odorant to the product is provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
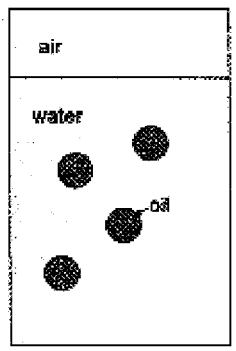
FIG. 1a is a graph of the partitions in a simplified oil in water emulsion.

This invention relates to methods of formulating fragrances and selecting odorants to be used within fragrances for products containing a nitrogen-based component or active agent. An odorants is selected based upon its ability to mask malodor caused by presence of ammonia and substituted amines. This ability is determined by the odorant's calculated mass transfer properties in emulsion partitions, and used to formulate fragrances to mask malodor. In addition, these odorants' conjugating properties to ammonia and other substituted amines based on electron orbital chemistry are used to determine the odorant's ability to cover malodor. Conjugation without bonding ammonia and amines is necessary as a method of limiting these malodor molecules' presence in the headspace without compromising the performance of the nitrogen-based product it is used within, such as hair colorants.

These methods can be applied to design fragrance to cover malodors present in various products. For example, such odorants can be used in various formulations stemming from cosmetic and personal care products such as depilatories, hair relaxants to household and industrial detergents which contain surfactant or active materials with a strong pungent smell. These specially designed fragrances can also be very efficacious in covering any other type of malodorants present in sweat and body odor, bathroom, kitchen and the like.

This invention deals primarily with the lowering of malodor inherent to hair coloring products, which contain a nitrogen-based component, and more specifically what are referred to as permanent, semi-permanent, demi-permanent hair colorants based on odorants mass transfer properties in various emulsion systems and their complexation properties in the presence of ammonia and various substituted amines.

According to the present invention, a fragrance or perfume composition is optimized for the coverage of nitrogen based malodor including ammonia and various substituted amines using odorants mass transfer properties and orbital chemistry. Odorants' partition release values are calculated as the product of the odorants' air impact, α and odorants' flux values φ out of the emulsion partition into the headspace. In addition, authors further consider odorants odor detection threshold values to further select for malodor coverage.

In addition to the above defined thermodynamic and mass transfer values, the fragrances may be designed by selecting odorants based on their ability of the odorants to conjugate ammonia and substituted amines without any covalent bond formation based on odorants electron orbital chemistry, and dipole moment values.

A. Thermodynamic and Mass Transfer Basis for Malodor Coverage

1. Air Impact α

Odorants' air impact is defined as the product of odorants vapor pressure, $P_v$ and diffusivity in air, $D_{air}$.

Vapor pressure is an important property in many practical applications. Vapor pressures are commonly used for assessing the mass distribution of chemicals in a defined environment, designing chemical processes and calculating other physicochemical properties such as enthalpy of vaporization, air-water partition coefficients, rates of vaporization, etc. Experimental vapor pressure data are abundant for low molecular weight hydrocarbons.

As a complement to experimental vapor pressure data, numerous correlation for estimating vapor pressures have been proposed. Most vapor pressure equations are either empirical or are based on the equation of state or on the Clausius-Clapeyron equation $$\frac{dP}{dT} = \frac{L}{T\Delta V},$$

with P, T, L and V respectively pressure, temperature, latent heat and volume. The Clayperon, Lee-Kesler, Riedel, Frost-Kwalkwarf-Thodos, Riedel-Plank-Miller and Thiek-Stiel are equations based on corresponding state relationships developed from critical temperature and pressure data.

Vapor pressure values are calculated based on odorants critical properties according to two methods: Frost Kalkwarf Thodos and the Miller semi-reduced methods. See K. Joback and R. Reid, Chem. Eng. Comm. 57: 233-243 (1987); A. L. Lydersen, Coll. Eng. Univ. Wisconsin. Eng. Expt. Sta. Rept. 3, Madison Wis., April, 1955; Entropy of boiling: P. Myrdal, J. Krzyzaniak, S. Yalkowsky, Ind. Eng. Chem. Res. 35:1788-92 (1996); Heat capacity change on boiling: P. Myrdal, S. Yalkowsky, Ind. Eng. Chem. Res. 36: 2494-99 (1997); Handbook of Chemical Property Estimation Methods, W. J. Lyman, W. F. Reed, D. H. Rosenblatt, McGraw Hill (1982).

Frost-Kalkwarf-Thodos Method

At temperature T and pressure P, the estimated vapor pressure $P_v$ of a volatile [defined by its critical properties: $T_c$ (critical temperature), $V_c$ (critical volume), and $P_c$ (critical pressure)] is given by the following equations:

$$\log(P) = \left(\frac{B}{T_c}\right) \cdot \left(\frac{1}{T_r} - 1\right) + \left(1.8\frac{B}{T_c} + 2.67\right). \quad [1]$$

-continued $$\log(T_r) + 0.1832 \cdot \left(\frac{P}{T_r^2} - 1\right)$$

with B given by:

$$B = \frac{-\log(P_c) - 2.67\log(\theta) + 0.1832 \cdot \left(1 - \frac{1}{P_c \cdot \theta^2}\right)}{\frac{1}{T_c} \cdot \left(\frac{1}{\theta} - 1\right) + \frac{1.8}{T_c} \cdot \log(\theta)} \quad [2]$$

$$P_v(atm) = P * P_c \quad [3]$$

With $$T_r = \frac{T}{T_c},$$

$P_c$ defined as the reduced temperature and critical pressure of the considered odorant, and $\theta$ as $$\theta = \frac{T_b}{T_c}$$

with $T_b$ the estimated and/or experimental boiling point value of the volatile.

Miller Semi-Reduced Method

At temperature T and pressure P, the estimated vapor pressure Pv of a volatile [defined by its critical properties: Tc (critical temperature), Vc (critical volume), and Pc (critical pressure)] is given by the following equations:

$$\log(P_v) = \frac{k}{T_r}[T_r^2(0.607T_r - 1.448) - (I_b \cdot T_r) - 0.98] \quad [4]$$

With $I_b$ defined as:

$$I_b = -1.448 \cdot \frac{\theta^2 - 1}{\theta} + 0.607 \cdot \frac{\theta^3 - 4}{\theta} \quad [5]$$

$$\theta = \frac{T_b}{T_c};$$

$T_b$ the boiling point of the volatile and k is given by:

$$k = \frac{H_c}{2.303 \cdot 1.987 \cdot T_c \cdot (1 - T_r)^{0.38}} \quad [6]$$

$H_c$ is defined as the corrected heat of vaporization according to Theisen-Fishtine method.

Diffusivity in Air, $D_{air}$ of odorants was calculated according to Slattery low pressure kinetic theory. See Advanced Transport Phenomena, John C. Slattery, Cambridge University Press, 1999. Air was assumed to be gas with specific critical properties. At pressure P and temperature T, the diffusivity of an odorant (A) in air (B) is given by $D_{AB}$:

$$\frac{P \cdot D_{AB}}{(P_{cA}P_{cB})^{1/3}(T_{cA}T_{cB})^{5/12}(1/M_A + 1/M_B)^{1/2}} = a\left(\frac{T}{\sqrt{T_{cA}T_{cB}}}\right) \quad [7]$$

and $T_{cA}$, $T_{cB}$, $M_A$, $M_B$ defined as respectively the critical temperatures of odorant and air and molecular weights of odorant and air.

The air impact of odorants is further defined as the product of odorant's estimated vapor pressure Pv in atm and the odorant diffusivity in air expressed in cm2/sec. The expression of air impact as defined by the authors is a measure of how well an odorant travels through an air partition or headspace, once liberated from an emulsion or a diluted medium. As an illustration, the defined air impact of some odorants is shown in the table below (Table 1):

TABLE 1

| Odorant | Air Impact |
| --- | --- |
| 2,6,6-trimethylbicyclo-(3,1,1)-2-heptene | 0.002024000 |
| 6,6-dimethyl-2-methylenebicyclo(3.1.1)heptane | 0.001110000 |
| isopropyl-methyl-2-butyrate | 0.001584000 |
| 7-methyl-3-methylene-1,6-octadiene | 0.000753300 |
| d-1-methyl-4-isopropenyl-1-cyclohexene | 0.000785600 |
| 2,6-dimethyl-2-heptanol | 0.000776500 |
| 1-methyl-4-isopropyl-1,5-cyclohexadiene | 0.000648600 |
| ethyl methanoate | 0.082000000 |
| ethyl acetate | 0.030000000 |
| diacetyl | 0.018000000 |
| ethyl propionate | 0.012000000 |
| ethyl butyrate | 0.004154000 |
| methyl hexyl ether | 0.003451000 |
| butyl acetate | 0.003424000 |
| hexanal | 0.003280000 |
| ethyl-2-methylbutyrate | 0.002954000 |
| β-methyl butyl acetate | 0.001758000 |
| pentyl acetate | 0.001632000 |
| tricyclodecenyl propionate | 0.000097480 |
| p-menth-1-en-8-yl acetate | 0.000057190 |
| cis-4-cyclopentadecenone | 0.000000452 |
| 5-cyclohexadecen-1-one | 0.000000416 |
| cyclopentadecenolide | 0.000000388 |

2. Flux, φ i. Partition Equilibrium

The effect of concentrations of odorant compounds on odor perception depends on their partial pressure $P_i$, over the emulsion matrix. This vapor pressure is determined at a fixed temperature (T), pressure (P) and chemical environment by the chemical potential ($\mu_i$) of the compounds:

$$\mu_i = \mu_i^0 + RT \ln a_i \quad [8]$$

where $\mu_i^0$ is the chemical potential in standard conditions. R is the perfect gas constant, and $a_i$ is the activity of the compound i (See Perez, J. Ph; Romulus, A. M. Thermodynamique. Fondements et Applications; Masson, Paris, France 1993).

This assumes equilibrium between three phases: the water phase, the oil phase and the gas phase, as shown in FIG. 1. The partitions considered are shown in FIG. 1 in simplified oil in water emulsion. (All flux calculations were done assuming 20% oil and 80% water. Values for flux will change according the content of oil in the partition.) At equilibrium, there is equality between the chemical potentials in the different phases:

$$a_{iw} = a_{io} \qquad [9]$$

$$\gamma_{iw} X_{iw} = \gamma_{io} X_{io} \qquad [10]$$

where $a_{iw}$ and $a_{io}$ are respectively, the activity of the compound i in water and oil phase; $\gamma_{iw}$ and $\gamma_{io}$ are respectively the activity coefficient in the water and oil phase, P is the total pressure, and $X_{iw}$ and $X_{io}$ are the molar fractions in water and oil phase, respectively. At constant concentration of the odorant in the emulsion, $X_{iw}$ and $X_{io}$ will change when the proportion of oil phase in the emulsion are modified.

If $P^{\infty}$ is the partition coefficient between the oil phase and the water phase and defined as:

$$P^{\infty} = \frac{C_o}{C_w} = \frac{K_w}{K_o} \qquad [11]$$

Hydrophobicity of an odorant or fragrance molecule can be measured using logP value, a physico-chemical property. The octanol/water partition coefficient (P) of a fragrance molecule is the ratio between its equilibrium concentrations in octanol and in water. Since the partitioning coefficients of the perfume ingredients of this invention have high values, they are more conveniently given in the form of their logarithm to the base 10, logP. The logP values can also be very conveniently calculated using the fragment approach of Hansch and Leo and given as clogP. See A. Leo, Comprehensive Medicinal Chemistry, Vol 4, C. Hansch et al. p 295, Pergamon press, 1990 and given as clogP. It is assumed by the authors that the following relationship is true:

$$10^{c\log P} \sim \frac{C_o}{C_w} \qquad [12]$$

$K_w$ can be obtained by estimating the concentration of odorant in headspace out of a straight water partition (water dilution) using the odorants calculated activity coefficient, and vapor pressure.

Buttery et al developed equations for determining the vapor/liquid partition coefficient K in three phase system (See Buttery, R. G., Guadagni, D. G., Ling, L. C., J. Agr. Food Chem. (1973), Vol 21, No. 2, 198-201). If K is defined as the ratio between the solute concentration in the air and the solute concentration in the mixture, with $K_w$ the air/water partition coefficient and $F_o$ and $F_w$ respectively, the volumetric fraction of oil and water in the mixture. K is given as:

$$K = \frac{K_w}{(F_w + F_o P^{\infty})} \qquad [13]$$

$K_w$ is known and determined as mentioned above, and $P^{\infty}$ can be estimated by equation [12].

The estimated concentration of odorant in headspace out the liquid (water/oil partition): $y_A$ is therefore given as a relationship between the odorant concentration in the emulsion $x_A$ and K:

$$y_A = K x_A \qquad [14]$$

ii. Flux $\phi$

For odorants with clogP less than 3.0, flux values were calculated as true flux values without including a factor for delay in the water partition. Flux of odorant (1) in emulsion partition (2) ($\phi_{12}$) is defined as the ratio of the quantity of odorant being transferred in the medium divided by the time and area of the contained medium.

Flux values can also be defined in relation to a concentration gradient of the odorant throughout an emulsion according to:

$$\phi_{12} = -D_{12}\left(\frac{d(c_1)}{dz}\right) \qquad [15]$$

where:

$D_{12}$ is the diffusion constant of odorant (1) in emulsion partition (2);

$$\left(\frac{d(c_1)}{dz}\right)$$

is the concentration gradient of odorant (1) throughout the partition.

Dimensionless Average Velocity $\upsilon$ of Odorant in Matrix

We wish to predict the time-dependent diffusion a volatile liquid odorant in a matrix resulting in its evaporation to headspace. We assume that the liquid level of the matrix remains constant at z=0 at all times. The dimensionless average molar velocity, v is given by the Arnold equation for non-steady state flux. See Arnold, J. H. *Trans A.I.ChE.*, 40,361-378 (1944).

$$1 + \left[(1 + \mathrm{erf}\,(\upsilon) \cdot \upsilon \cdot \exp(\upsilon^2) \cdot \sqrt{\pi}\,\right] = \frac{1}{yA} \qquad [16]$$

The error function erf is defined as $$\mathrm{erf}\,x = \frac{\int_0^x \exp(-\bar{x}^2)\,d\bar{x}}{\int_0^\infty \exp-(\bar{x}^2)\,d\bar{x}} = \frac{2}{\pi}\int_0^x \exp(-\bar{x}^2)\,d\bar{x} \qquad [17]$$

This function, arises naturally in numerous transport problems, is monotone, increasing going from erf (0)=0 and $\mathrm{erf}\infty=1$, and has the value of 0.99 at about x=2 and some properties of this function include $-\mathrm{erf}(-\phi)=\mathrm{erf}\phi$ and $\mathrm{erf}\infty=1$.

Flux $\phi$

The volume rate of vapor production ($V_a$) at time t for evaporation from a surface of diameter (dia) is $$V_a = \left[\pi\frac{(2.54 dia)^2}{4}\right] \cdot \upsilon \cdot \sqrt{4(D_{12} + E)t} \qquad [18]$$

$D_{12}$: calculated diffusion coefficient of the odorant A in the matrix B and E: eddy diffusion The addition of eddy diffusion is used to include mixing at the surface, and translates the contribution of the molecular velocity of water vapor sweeping the surface. E is calculated to be equal to be 6.974 (10-4) for water.

As an example, for oil in water emulsion, D12 is defined as the diffusion coefficient of odorant 1 in the matrix 2 also thought as water/vapor in water based emulsions. It is calculated the Slattery kinetic theory for water with non polar odorants based on equation:

$$D_{12} = \frac{\left[3.640\,(10^{-4})\left(\frac{T}{\sqrt{T_{c1}T_{c2}}}\right)^{2.334}\right]\left[(P_{c1}P_{c2})^{\frac{1}{3}}(T_{c1}T_{c2})^{\frac{5}{12}}\left(\frac{1}{M_1}+\frac{1}{M_2}\right)^{\frac{1}{2}}\right]}{P_{atm}} \quad [19]$$

$T_c$, $P_c$ are the critical temperatures and pressures of both odorant and water and $M_1$ and $M_2$ the mass weights for odorant and water. The mass flux [mg/sec*area] is calculated using the area:

$$\left[\pi\frac{(2.54 \cdot dia)^2}{4}\right]$$

The compressibility corrected ideal gas equation is used to convert volume to moles:

$$n(moles) = \frac{P_a V_a}{82.056 TZ} \quad [20]$$

The mass flow rate of odorant per unit area (or mass flux) for odorants becomes:

$$\phi = \frac{P_a \cdot v \cdot \left(\sqrt{4 \cdot (D_{ab}+E) \cdot t}\right)}{t[82.056TZ]} MW \quad [21]$$

For odorants with clogP higher than 3.0, a delayed flux calculation is assumed the emulsion partition. A delay-flux value is derived based on the Arnold equation with the inclusion of a delay time based on the empirical observation that improved ammonia and general nitrogen based malodor coverage is proportional to clogP value of odorants. This delay is calculated from the same Arnold equation and is the time for the concentration in the headspace to reach 50% of its equilibrium value (this concentration is arbitrary). First order diffusion is also assumed in this case. See Bird-Stewart-Lightfoot: Transport Phenomena 1960 (1st edition) Wiley and Sons p 601. The odorant is assumed to diffuse from the source at a rate dependent on the relative diffusivities. This dependence is also based on first order kinetics.

The delay time is based steady state assumption and derived as explained in Bird-Stewart-Lightfoot: Transport Phenomena 1960 (1st edition) Wiley and Sons p 595. It represents the time for the odor concentration to reach 50% of its equilibrium value at a distance of 1 cm from the source. It is obtained by:

$$t = \frac{1}{4D_{12}}\left(\frac{1}{\Lambda}\right)^2 \quad [22]$$

and $\Lambda$ is obtained by solving the following error function since $\phi$, the dimensionless average molar velocity is calculated according to equation [14]:

$$0.5 = \frac{1 - \mathrm{erf}(\Lambda - \phi)}{1 + \mathrm{erf}(\phi)} \quad [23]$$

Examples of flux values for various odorants calculated using the method shown above and assuming oil in water emulsion partition with an arbitrary oil content of 20% are shown in table 2.

TABLE 2

| Odorant | Flux |
|---|---|
| ethyl-2-methylbutyrate | 7.86E−07 |
| cis-4-heptenal | 5.03E−07 |
| prenyl acetate | 3.82E−06 |
| ethyl 2-methyl-1,3-dioxolane-2-acetate | 1.04E−06 |
| hexyl formate | 8.55E−08 |
| methyl-2-octynoate | 1.45E−09 |
| d-1-Methyl-4-isopropenyl-1-cyclohexene | 9.27E−06 |
| 2,6-Dimethyl-2-heptanol | 8.38E−06 |
| 1-Methyl-4-isopropyl-1,5-cyclohexadiene | 9.39E−06 |
| 2-ethenyl-2,6,6-trimethyltetrahydropyran | 8.21E−06 |
| 1-Methyl-4-isopropyl-1,4-cyclohexadiene | 9.17E−06 |

3. Rationale for High Flux and Air Impact Odorants in Coverage of Ammonia

Ammonia has a very high rate of diffusion out of emulsion partition due to its extremely high volatility and air diffusion coefficient. It is usually introduced as a solution of ammonia hydroxide, $NH_4OH$ (29% solution) in concentrations generally ranging from 1-15% by weight of the product. For instance, with reference to hair coloring products, ammonia hydroxide generally may comprise up to 10% by weight of the product for lighter shade colorations. The liberated ammonia $NH_3$ is characterized by a sharp odor, which is very challenging to cover due to the very extreme characteristics of ammonia mentioned above. Substituted amines, on the other hand are much less disagreeable and easier to cover although more potentially more reactive than ammonia and therefore more challenging from a stability point of view due to the potential Schiff Base formation in presence of aldehydes and some non saturated ketones.

Covering ammonia malodor and to a lesser degree substituted amines has to due mostly with the "slowing down" of these malodors while allowing the odorants in the perfume to populate the headspace. Selecting odorants with very high values for air impact $\alpha$ and flux $\phi$ will therefore be one goal of this invention. Odorants identified by the inventors as having good ammonia coverage solely based on their diffusion out of the oil/water partition and subsequent diffusivity in air must have a value of the product of their flux ($\phi$) and air impact ($\alpha$) of about $5 \times 10^{-13}$ or greater.

Once in headspace, odorants are detected based on their odor detection threshold values. Odor detection thresholds are defined as the lowest concentration of odorants in a selected medium (air or water) to be detected. By including odor detection thresholds of odorants in the model, one can further improve on the values for predicted performance of once odorants are released from the partition into the air. Various databases for experimental odor detection threshold values in various partitions such as water and air are available. See Compilation of Odor and Taste Threshold Values Data, American Society for Testing and Materials, F. A. Fazzalari Editor; Booleans Aroma Chemical Information Service (BACIS))

Some of these high flux and high air impact odorants with low odor detection threshold values are shown below in Table 3.

TABLE 3

| Odorant | Air Impact | Flux | ODT (ppb) |
|---|---|---|---|
| ethyl propionate | 1.20E−02 | 4.90E−04 | less than 50 ppb |
| ethyl butyrate | 4.15E−03 | 1.39E−05 | less than 50 ppb |
| methyl hexyl ether | 3.45E−03 | 3.24E−07 | less than 50 ppb |
| hexanal | 3.28E−03 | 8.74E−06 | less than 50 ppb |
| ethyl-2-methylbutyrate | 2.95E−03 | 7.86E−07 | less than 50 ppb |
| ethyl 3-methylbutanoate | 2.90E−03 | 9.20E−07 | less than 50 ppb |
| β-methyl butyl acetate | 1.76E−03 | 3.96E−07 | less than 50 ppb |
| pentyl acetate | 1.63E−03 | 3.36E−07 | less than 50 ppb |
| propyl butyrate | 1.57E−03 | 4.14E−07 | less than 50 ppb |
| cis-4-heptenal | 1.12E−03 | 5.03E−07 | less than 50 ppb |
| ethyl 2-methyl-1,3-dioxolane-2-acetate | 1.07E−03 | 1.04E−06 | less than 50 ppb |
| ethyl 2-methylpentanoate | 8.47E−04 | 1.32E−08 | less than 50 ppb |
| 1,3,3-trimethyl-2-oxabicyclo[2.2.2]octane | 6.58E−04 | 1.07E−08 | less than 50 ppb |
| ethyl hexanoate | 6.07E−04 | 6.46E−09 | less than 50 ppb |
| hexyl acetate | 5.44E−04 | 3.89E−09 | less than 50 ppb |
| 3-octanone | 5.39E−04 | 7.01E−08 | less than 50 ppb |
| cis-3-hexenol | 4.84E−04 | 5.75E−07 | less than 50 ppb |
| 2,6-dimethyl-5-heptenal | 2.64E−04 | 1.23E−09 | less than 50 ppb |
| cis-3-hexenyl methyl carbonate | 2.49E−04 | 7.90E−09 | less than 50 ppb |
| methyl cyclopentylidene acetate | 2.43E−04 | 4.61E−09 | less than 50 ppb |

Odorants identified by the inventors as having good ammonia coverage solely based on their diffusion out of the oil/water partition and subsequent diffusivity in air may have a value of the product of their flux ($\phi$) and air impact ($\alpha$) equal to about $5 \times 10^{-13}$ or greater. Preferably, odorants with values of the product of flux and air impact as mentioned previously may additionally have odor detection threshold values in water of about 50 parts per billion or less.

Odorants identified as having high flux and high air impact values include but are not limited to: ethyl formate, ethyl acetate, diacetyl, ethyl propionate, ethyl butyrate, methyl hexyl ether, hexanal, ethyl-2-methyl-butyrate, ethyl-3-methyl-butyrate, isopentyl ethanoate, β-Methyl butyl acetate, n-Pentyl ethanoate, E-2-hexenal, propyl butyrate, Phenyl methyl ether, cis-4-heptenal, 3-methyl-2-butenyl acetate, ethyl 2-methyl-1,3-dioxolane-2-acetate, hexyl formate, ethyl 2-methylpentanoate, cis-3-hexenyl formate, 1,3,3-Trimethyl-2-oxabicyclo[2.2.2]octane, ethyl caproate, 6-methyl-5-hepten-2-one, trans-2-hexenyl acetate, hexyl acetate, 3-Octanone, trans-2-hexenol, benzaldehyde, cis-3-hexenol, phenylethyl methyl ether, octanal, Bicyclo[2.2.1]heptan-2-one, 1,3,3-trimethyl, 1-phenylethyl acetate, ethyl acetoacetate, 2,6-Dimethyl-5-heptenal, cis-3-hexenyl methyl carbonate, Methyl cyclopentylidene acetate, Dimethylcyclohex-3-ene-1-carbaldehyde, phenylacetaldehyde, 3,6-Dihydro-4-methyl-2-(2-methylpropen-1-yl)-2H-pyran, d-1,7,7-Trimethylbicyclo[2.2.1]heptan-2-one, 1-Ethyl-3-methoxytricyclo[2.2.1.02,6]heptane, 2-phenylpropanal, 1-(3,3-Dimethylcyclohexyl)ethan-1-one, 1-Octen-3-ol, 3-octanol, cis-3-hexenyl acetate, 3,7-dimethyl-7-methoxyoctan-2-ol, Ethyl propanedioate, 3-phenyl butanal, p-cresyl acetate, Nona-2-trans-6-cis-dienal, benzyl acetate, 2-methyl-3-(4-methoxyphenyl)propanal, 3-phenylpropanal, 4-methoxyacetophenone, methyl-2-octynoate, 4-hydroxy-3,5-dimethoxybenzaldehyde, 2-Methylpent-2-en-1-oic acid, 2-Methyl-4-propyl-1,3-oxathiane, 1-phenylethyl alcohol, phenylacetaldehyde, α-hydroxytoluene, Ethyl 2,4-dimethyl-dioxolane-2-acetate, γ-n-Butyl-g-butyrolactone, phenylethyl formate, γ-nonalactone, butyl butyrate, 2,6,6-Trimethylbicyclo-(3,1,1)-2-heptene, 6,6-Dimethyl-2-methylenebicyclo(3.1.1)heptane, isopropyl-methyl-2-butyrate, 7-Methyl-3-methylene-1,6-octadiene, (R)-(+)-p-Mentha-1,8-diene; d-1-Methyl-4-isopropenyl-1-cyclohexene, 2,6-Dimethyl-2-heptanol, p-Mentha-1,5-diene; 1-Methyl-4-isopropyl-1,5-cyclohexadiene, 2-ethenyl-2,6,6-trimethyltetrahydropyran, 1-Methyl-4-isopropylidene-1-cyclohexene, trans,trans-2,6-Dimethyl-2,4,6-octatriene, 2,2-Dimethyl-3-(3-methyl-2,4-pentadienyl)oxirane, Tetrahydro-4-methyl-2-(2-methylpropen-1-yl)pyran, methyl-2,2-dimethyl-6-methylene-1cyclohexanecarboxylate, cis-4-hexahydrocuminyl alcohol, Isobutyl cis-2-methyl-2-butenoate, 3-Methylbutyl butanoate, 1,3-Dimethylbutyl 2-butenoate, 2-Methylhendecanal, 2-Propenyl hexanoate, nonanal, 4-(1-Methoxy-1-methylethyl)-1-methylcyclohexene, tricyclodecenyl acetate, ethyl heptanoate, 2-Methyl-1,5-dioxaspiro[5.5]undecane, cis-3-hexenyl isobutyrate, 1,3,5-Undecatriene, 1,3-Dimethylbut-3-enyl isobutyrate, 3,7-Dimethyloctanal, butyl 2-methyl pentanoate, E-4-Decenal, 1,3-undecadien-5-yne, Z-6-nonenal, citronellyl nitrile, 3,7-Dimethyl-1,6-octadien-3-ol, Tricyclodecenyl propionate, o-t-butylycyclohexyl acetate.

More specifically high flux and high air impact odorants with odor detection threshold values of about 50 parts per billion or less include,are not limited to, diacetyl, ethyl butyrate, methyl hexyl ether, ethyl-2-methyl-butyrate, isopentyl ethanoate, β-Methyl butyl acetate, n-Pentyl ethanoate, propyl butyrate, cis-4-heptenal, 3-methyl-2-butenyl acetate, ethyl 2-methyl-1,3-dioxolane-2-acetate, ethyl 2-methylpentanoate,1,3,3-Trimethyl-2-oxabicyclo[2.2.2]octane, ethyl caproate, hexyl acetate, 3-Octanone, cis-3-hexenol, 2,6-Dimethyl-5-heptenal, cis-3-hexenyl methyl carbonate, Methyl cyclopentylidene acetate, Dimethylcyclohex-3-ene-1-carbaldehyde,1-Ethyl-3-methoxytricyclo[2.2.1.02,6]heptane, 1-Octen-3-ol, cis-3-hexenyl acetate, 3-phenyl butanal, p-cresyl acetate, Nona-2-trans-6-cis-dienal, benzyl acetate, methyl-2-octynoate, 2-Methyl-4-propyl-1,3-oxathiane, γ-n-Butyl-g-butyrolactone, γ-nonalactone, (R)-(+)-p-Mentha-1, 8-diene; d-1-Methyl-4-isopropenyl-1-cyclohexene, 2,2-Dimethyl-3-(3-methyl-2,4-pentadienyl)oxirane, Tetrahydro-4-methyl-2-(2-methylpropen-1-yl)pyran, methyl-2,2-dimethyl-6-methylene-1cyclohexanecarboxylate, 2-Propenyl hexanoate, tricyclodecenyl acetate, butyl 2-methyl pentanoate, E-4-Decenal, 1,3-undecadien-5-yne, Tricyclodecenyl propionate, o-t-butylycyclohexyl acetate.

B. Malodor Conjugating Odorants

1. Ammonia and Substituted Amines Orbital Chemistry

Generally, hair Coloring products contain ammonia in permanent coloring products and substituted amines in semi-permanent formulations. Various combinations of ammonia and amines may be present simultaneously in some products such as demi-permanent hair colorants. It important to note that conjugation of ammonia and substituted amines by specific odorants is made possible by the electron orbital structure of these compounds.

Ammonia, $NH_3$ is considered a weak base with very strong nucleophilic tendencies based on the lone pair of electrons shown in figures below. All displayed surfaces were calculated according to PM3 method based on the Neglect of Diatomic Differential Overlap (NDDO) approximate Hamiltonian (See Ground States of Molecules. 38. The MNDO Method. Approximations and Parameters", Dewar, M. J. S. and Thiel, W. J. Am. Chem. Soc., 1977, 99, 4899-4907; "AM1: A General Purpose Quantum Mechanical Molecular Model", M. J. S. Dewar, E. G. Zoebisch, E. F. Healy, and J. J. P. Stewart, J. Am. Chem. Soc., 1985, 107, 3902-3909; "Optimization of Parameters for Semi empirical Methods II. Applications", Stewart, J. P. J. J. Computational Chemistry, 1989, 10, 221-264.

Figure 1B:
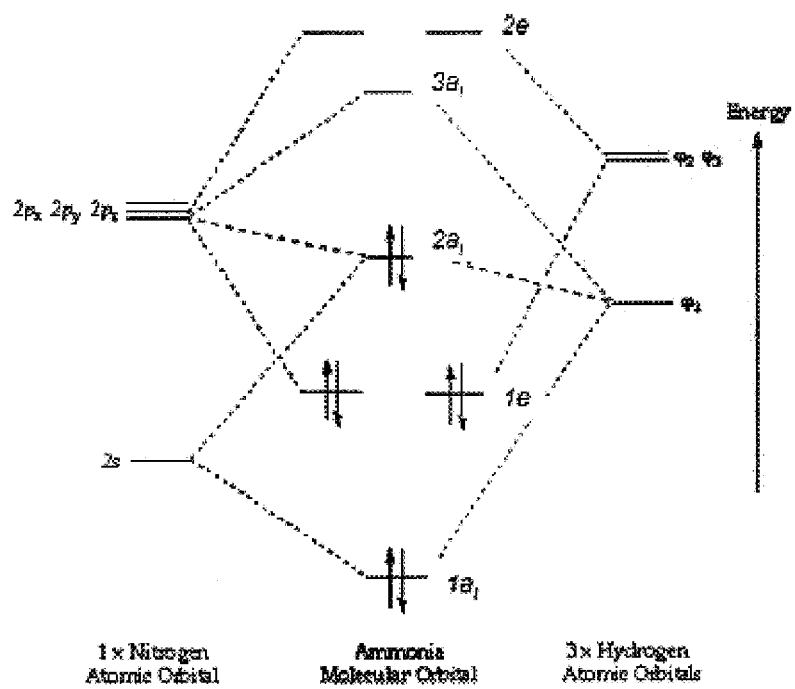
FIG. 1b shows the orbital structure for ammonia.

As shown in FIG. 1b, ammonia has two pairs of degenerate orbitals, one bonding and one antibonding, and a non-bonding orbital ($2a_1$). This highest occupied orbital has a lobe pointing away from the three hydrogens (see FIG. 1b), and corresponds to a lone pair orbital localized upon the nitrogen, whereas the three lowest energy MO's lead to the description of the three N—H bonds of the Lewis structure. The lone pair is relatively high in energy, and is responsible for the well known Lewis base properties of ammonia.

Figure 2:
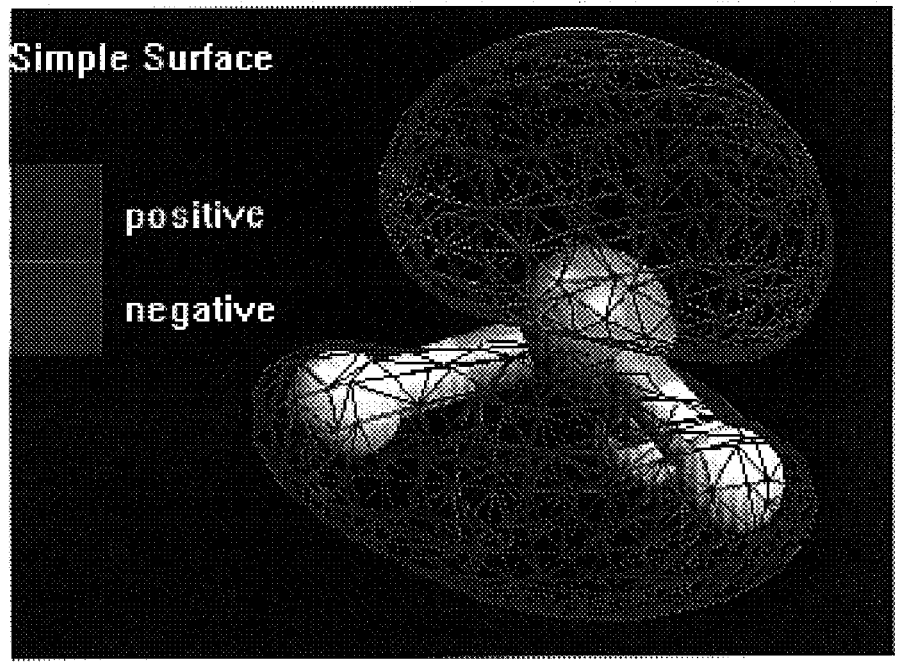
FIG. 2 shows surface display for ammonia Highest Occupied Molecular Orbital ("HOMO") Orbital.

In FIG. 2, the Highest Occupied Molecular Orbital surface map for ammonia is shown. (Negative charges are coded red and positive charge coded white.) A contour is a line in two-dimensional space which connects points having a particular value of a wavefunction. The eigenvalue for the HOMO orbital is calculated to be −0.379125 au. The eigenvalues for the LUMO orbital of ammonia is calculated to be 0.119813 au.

2. Dipole Moments

Figure 3:
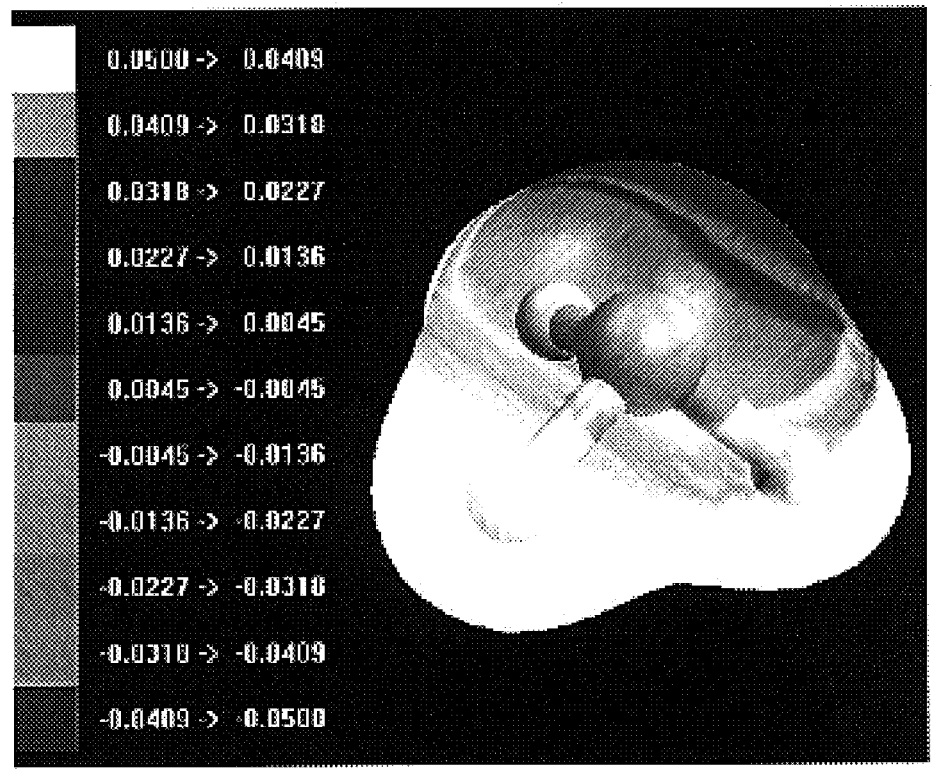
FIG. 3 is an electrostatic potential ("ESP") density map of ammonia.

Dipole moment is a measure of the distribution and strength of partial charges in a molecule. Some molecules have apparent negative and positive poles. Molecules with the mean distribution of partial charge towards one side of the molecule will have a higher dipole moment than a molecule with centralized mean charge distribution. For instance, ammonia, has a strong dipole moment as shown by its electrostatic potential ("ESP") mapped on a surface of electron density. (See Electrostatic Potential ("ESP") map shown at FIG. 3). The electron density surface gives the shape of the surface while the value of the ESP on that surface gives the color, with red coded for negative and blue coded for positive. The ESP density surface was calculated using a PM3 Hamiltonian from Argus Software (Planaria Software). These ESP maps are used to visualize the electrostatic properties of molecules throughout the herein invention and help visualize the dipole moments.

Since dipole moments are a function of distance and charge the units of measure contain terms for charge and distance. For instance 1 debye=$1\times10^{-18}$ esu cm (where $4.8\times10^{-10}$ esu=$1.6\times10^{19}$ coulombs)

Odorants were minimized based on a force-field based approach using the UFF force field. Geometry optimization calculation is run to convergence. See UFF, a Full Periodic Table Force Field for Molecular Mechanics and Molecular Dynamics Simulations", A. K. Rappe', C. J. Casewit, K. S. Colwell, W. A. Goddard III, and W. M. Skiff. J. Am. Chem. Soc., 1992, 114, 10024-10035. "Application of a Universal Force Field to Organic Molecules", C. J. Casewit, K. S. Colwell, and A. K. Rappe', J. Am. Chem. Soc., 1992, 114, 10035-10046. "Application of a Universal Force Field to Metal Complexes", A. K. Rappe', K. S. Colwell, and C. J. Casewit, Inorg. Chem., 1993, 32, 3438-3450. All odorants hybridizations were cleaned using the Extended Huckel method (EHT) (See "Quantum Chemistry", John P. Lowe, Academic Press, 1978, ISBN 0-12-457552-8, (chapter 10).

Partial charges are the charges assigned to each atom. These are theoretical values that have never been experimentally measured (many experimental values for dipole moment do exist though. The software Molecular Modeling Pro was used calculate the dipole moment from the partial charges of the individual atoms. The program uses a modified version of DelRe's method for calculating partial charge, or uses CNDO, INDO or extended Huckel calculations. The modified DelRe method use the same mathematical method as DelRe, but has modified the parameter values so that more atom types are covered, and the results of conformationally rigid molecules give dipole moments like those reported in the literature. This program takes into account some pi bonding as well as sigma bonding. The program finds the deviation of charge location from the mean x, y and z atom coordinate values, then finds dipole moment from the x, y and z components. For some structure-activity studies the x, y and z dipole component values may have more meaning than the overall dipole moment, especially if you have taken care to orient all the molecules in a data base in the same way. (see G. Del Re, J. Chem. Soc. (1958) pps 4031-4040; G. Del Re, Biochem. et Biophys. Acta 75:153-182 (1963); D. Polland and H. Sheraga, Biochemistry 6:3791-3800 (1967).

CNDO is a semi-empirical quantum chemistry program used to calculate partial charges and dipole moments. CNDO stands for 'Complete neglect of differential overlap'. It is less rigorous then MNDO. Both programs are known as semi-empirical because they are based on a mixture of first principles of chemistry and physics with experimental results that are used to determine the Hamiltonians. Programs doing quantum chemistry based only on first principles are known as 'ab-initio' calculations. CNDO uses two main approximations that deviate from ab-initio: a) a core approximation and b) the zero-differential overlap approximation. CNDO and MNDO are examples of "Self consistent field theory", which obtain the results by solving simultaneous non-linear equations iteratively until the results between two iterations are close. CNDO calculates pure wave functions based on atom location and atom type only.

The point-charges on the ammonia molecule are shown below in Table 4.

TABLE 4

| Atom | Del Re | PEOE + Huckel/4 | MPEOE |
| --- | --- | --- | --- |
| N1 | −0.8771929 | −0.3436872 | −0.4832102 |
| H2 | 0.2923976 | 0.1145624 | 0.1610701 |
| H3 | 0.2923976 | 0.1145624 | 0.1610701 |
| H4 | 0.2923976 | 0.1145624 | 0.1610701 |

The net charge distribution on the ammonia molecule results in a one-axis directional dipole of approximately 1.47 D. The same type of overall polarity holds true for all substituted aliphatic amines such as ethylamine etc.

Part of this invention deals with choosing odorants capable of "softly" interacting with ammonia and other substituted aliphatic nitrogen compounds via dipole-dipole interactions without chemically reacting with them. These dipole-dipole interactions are between odorants with permanent dipoles and the malodor molecule's dipole. In instances of interaction between ammonia and other substituted amine compounds and odorants with strong dipole moments, interactions called hydrogen bonds may arise. In addition, these odorants with strong dipole moments must also have a clogP value of about 4.0 and greater. Calculation of clogP depends upon the oil to water ratio of the product emulsion, and has been calculated upon the ratio of 20:80 which is generally applicable to products such as hair colorants for instance.

As an illustration, β-1-(2,6,6-trimethyl-1-cyclohexen-1-yl)-2-buten-1-one (β-damascone) is used for its excellent ability to complex ammonia. Its boiling point and clogP values are respectively 260° C. and 4.42. Its odor detection threshold value in water is 0.09 parts per billion. As part of larger stability and evaluation study done at room temperature (RT) and in the oven at 37° C., for potential malodor coverage odorants, β-damascone's performance in an ammonia formulation (10% ammonia) is shown below in Table 5. The marks E, VG, G stand for excellent, very good and good coverage and are part of a 5 scale rating system.

TABLE 5

| 1 Week | | 2 Weeks | | 3 Weeks | | 4 Weeks | | 5 Weeks | | 6 Weeks | |
|---|---|---|---|---|---|---|---|---|---|---|---|
| RT | Oven | RT | Oven | RT | Oven | RT | Oven | RT | Oven | RT | Oven |
| E | VG | E | VG | VG | G | VG | G | VG | G | G | G |

Figure 4:
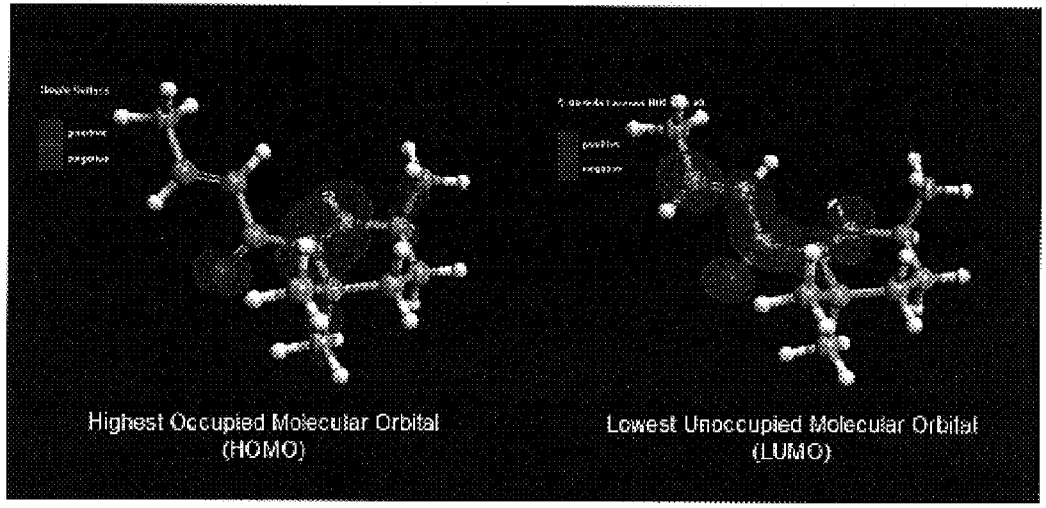
FIG. 4 shows HOMO and Lowest Occupied Molecular Orbital ("LUMO") contour maps of β-damascone.
Figure 5:
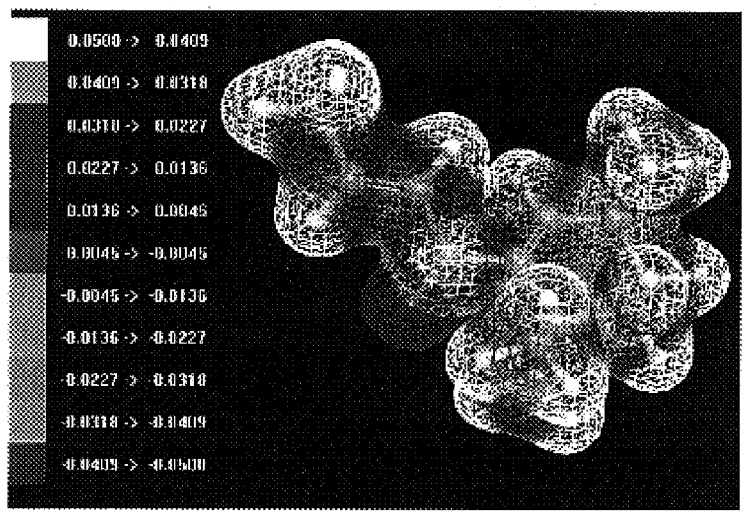
FIG. 5 is an ESP density map of β-damascone

The structure of β-damascone is shown in FIG. 4, along with its HOMO and LUMO contour maps (Negative charges are coded red and positive charge coded white.) The eigenvalues for HOMO (MO 39) and LUMO (MO 40) orbitals were found to be −0.366427 (au) and −0.012321 (au) respectively. The electron density map of β-damascone in FIG. 5 shows a very strong dipole moment.

Figure 1C:
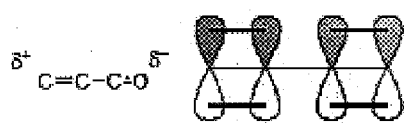
FIG. 1c shows a first electron resonance structure for the chemical class of β-enones.

The π-electron systems of the two functional groups are conjugated (the pi-orbitals overlap in space), as shown in FIG. 1c. All the double bond P-orbitals overlap. There is a second resonance form shown in FIG. 1d. The C=C is polarised, with net δ+ on the terminal carbon, further creating a more pronounced dipole moment (see FIG. 5).

Figure 6:
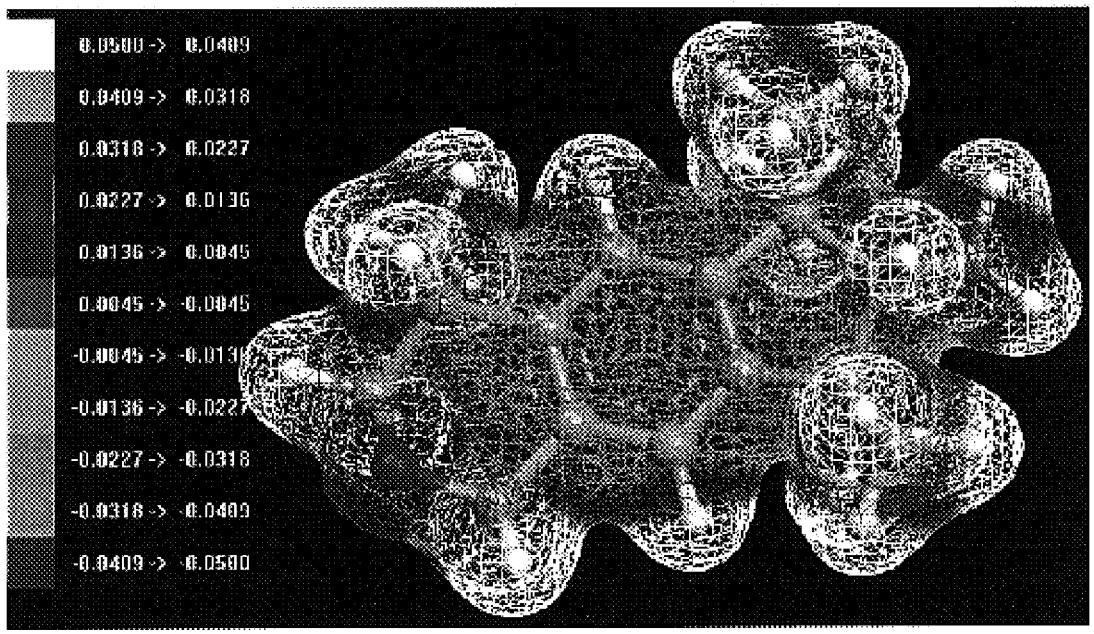
FIG. 6 is an ESP density map of galaxolide

In addition, Benzene rings and other aromatic systems can display dipole characteristics and further with hydrogen bond donors such as NH. (See Levitz, M. Perutz, M. F. J. Mol. Biol. (1988) 201, 751-754). The NH . . . π facial interactions present an example of non-classical H bond interaction that can also help slow down the entrance of ammonia into headspace. As an example, the electron density map of Galaxolide, very good ammonia and amine malodours covering odorant is shown in FIG. 6. Its performance in a 10% ammonia hair colorant creme is shown below in Table 6.

TABLE 6

| 1 Week | | 2 Weeks | | 3 Weeks | | 4 Weeks | | 5 Weeks | | 6 Weeks | |
|---|---|---|---|---|---|---|---|---|---|---|---|
| RT | Oven | RT | Oven | RT | Oven | RT | Oven | RT | Oven | RT | Oven |
| E | E | VG | VG | G | G | G | G | G | G | G | G |

Odorants identified by the authors to conjugate ammonia and other amine based malodors according to their ability to form dipole-dipole interactions with ammonia and substituted amines as described above and in case of some, can either be hydrogen bond donors and/or acceptors. Odorants capable of complexing ammonia and other substituted amine compounds must have a clogP of about 4.0 and greater and display strong dipole moments with values of about 1.5 debye or greater as calculated by the Del-Re method and have an a hydrogen bond donor and/or acceptor index of about 0.1 and greater. These odorant belong to chemical classes as illustrated but not limited to the examples shown below:

Examples of Cyclopentanone Derivatives are 9-cycloheptadecen-1-one (civettone), 3-methylcyclopentadecanone (muscone), 5-cyclohexadecen-1-one (ambretone), cyclopentadecanone (exaltone), oxacycloheptadec-10-en-2-one (ambrettolide), 2-[2-(4-Methylcyclohex-3-en-1-yl)propyl]cyclopentanone (nectaryl), (4R-(4α,4aα,6β))-4,4a,5,6,7,8-Hexahydro-4,4a-dimethyl-6-(1-methylvinyl)naphthalen-2(3H)-one (Nootkatone) etc.

Figure 7:
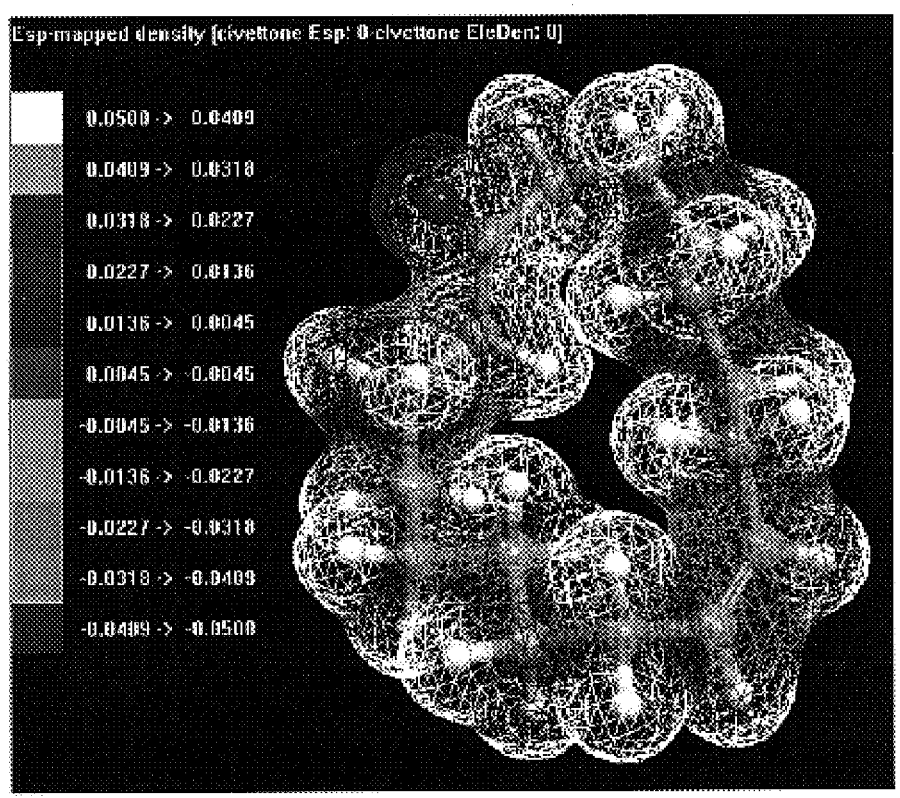
FIG. 7 is an ESP density map of 2Civetone.

As an example, civetone electron density map (ESP map) is shown in FIG. 7. In addition, the dipole moment of civetone is estimated using a Del-Re method and shown below, along with its hydrogen bond acceptor index:

| Civetone dipole moment |
|---|
| Dipole moment (Modified Del Re): |
| x component: 4.269615E−02 |
| y component: 4.816484E−02 |
| z component: −0.5461516 |
| Total = 2.63967 debyes |
| = 8.80593877029419 × 10$^{\wedge}$−30 C m | hydrogen bond acceptor = 0.2647909
hydrogen bond donor =

Phenyl Compounds have a phenyl ring and a conjugated π orbital system capable of π-NH facial hydrogen bonding interactions. Examples of these compounds are 1,3,4,6,7,8-Hexahydro-4,6,6,7,8,8-hexamethylcyclopenta-γ-2-benzopyran (Galaxolide), 4-Acetyl-6-t-butyl-1,1-dimethylindan (Celestolide), trans-2,4-Dimethyl-2-(5,6,7,8-tetrahydro-5,5,8,8-tetramethyl-2-naphthalenyl)-1,3-dioxolane (okoumal).

The ESP density map representation for galaxolide is shown in FIG. 6 and with its dipole moment calculation is summarized below:

| Galaxolide dipole moment |
|---|
| Dipole moment (Modified Del Re): |
| x component: 0.1521132 |
| y component: 6.413169E−03 |
| z component: −0.3749579 |
| Total = 1.942506 debyes |
| = 6.4802002658844 × 10$^{\wedge}$−30 C m | hydrogen bond acceptor = 0.1647448
hydrogen bond donor = 8.839831E−03

Figure 8:
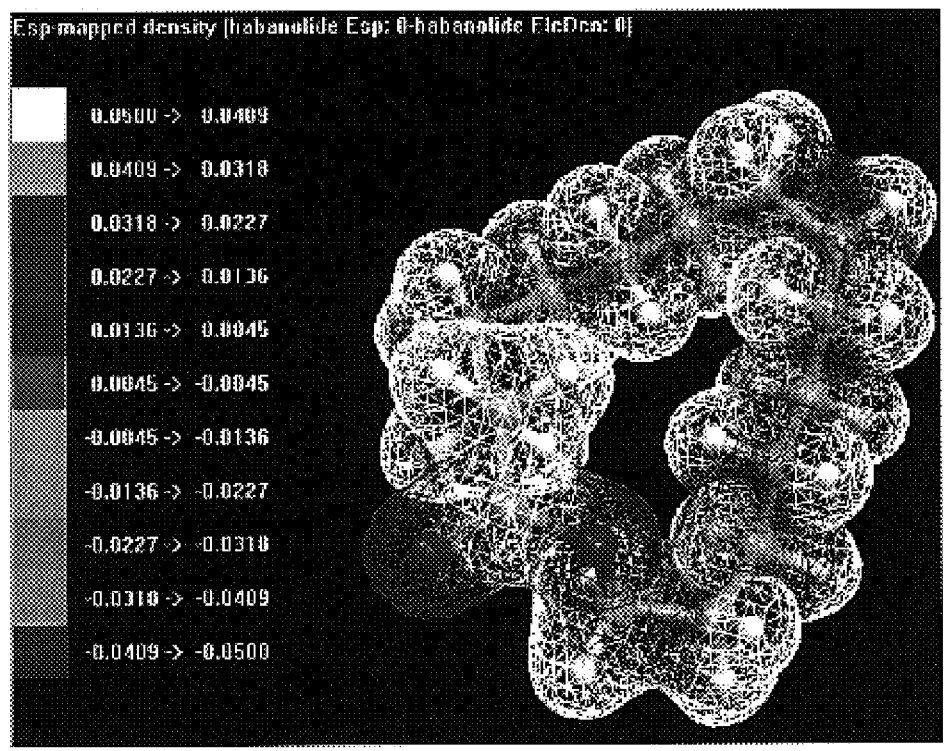
FIG. 8 is an ESP map for habanolide.

High molecular weight lactones and aliphatic esters such as habanolide (cyclopentadecenolide) are also thought to interact with ammonia and substituted amines. The ESP density map of habanolide is shown in FIG. 8. A summary of the dipole moment calculation for habanolide is as follows:

| Habanolide dipole moment |
|---|
| Dipole moment (Modified Del Re): |
| x component: 0.2173167 |

-continued

| Habanolide dipole moment |
|---|
| y component: 0.1717391
z component: 0.2854861
Total = 1.909309 debyes
= 6.36945611572266 × 10^−30 C m | hydrogen bond acceptor = 0.3124799
hydrogen bond donor =

Figure 9:
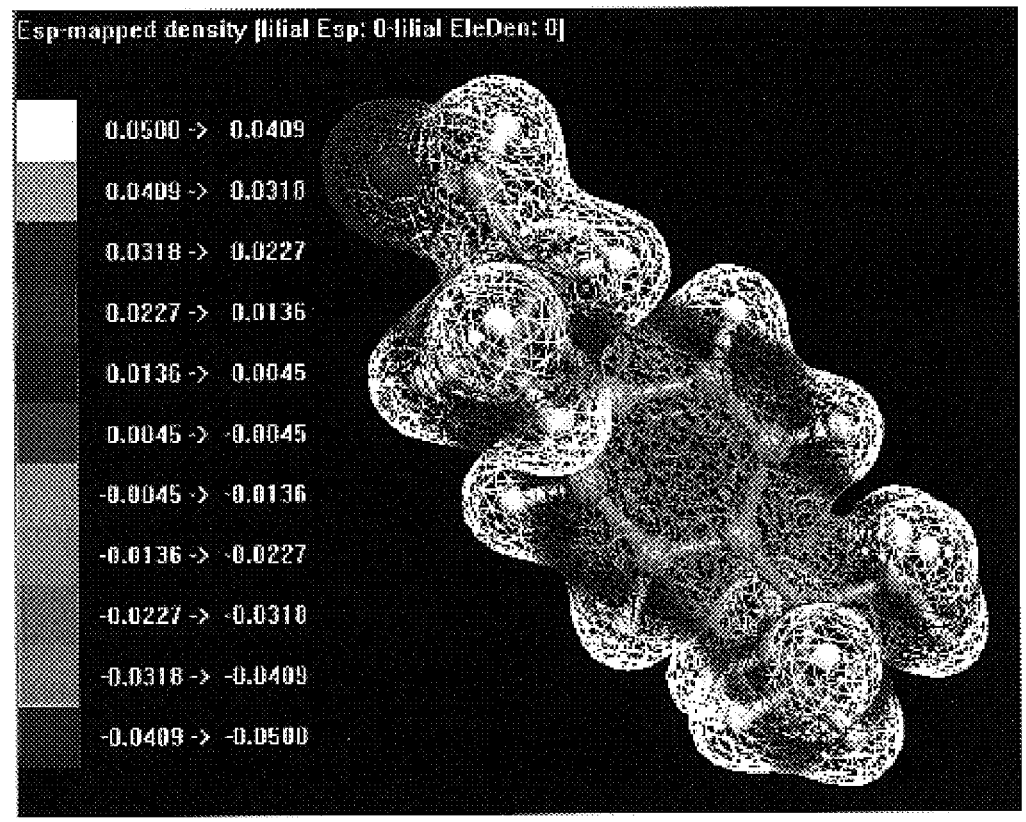
FIG. 9 is an ESP map for lilial.

Aryl alkyl cinnamic aldehydes are also very good ammonia and substituted amines covering agents. Some examples which belong to this group of chemicals are p-Isobutyl-α-methyl hydrocinnamaldehyde (silvial, rhodial), p-t-Butyl-α-methylhydrocinnamic aldehyde (lilial). The ESP map for lilial is shown in FIG. 9. The dipole moment calculation for lilial is as follows:

| Lilial dipole moment |
|---|
| Dipole moment (Modified Del Re):
x component: −0.4735285
y component: −0.3684373
z component: 7.566914E−02
Total = 2.902715 debyes
= 9.6834563369751 × 10^−30 C m | hydrogen bond acceptor = 0.179365
hydrogen bond donor = 3.564227E−02

Figure 1D:
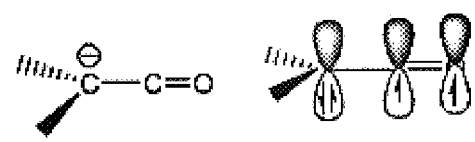
FIG. 1d shows a second electron resonance structure for the chemical class of β-enones.

Odorants belonging to the chemical class referred to as β-enones are compounds in which a carbonyl (keto) is bonded to a carbon-carbon double bond. These odorants have the following functional group: C=C—C=O. These odorants present a strong dipole moment as shown in FIGS. 1c and 1d π-electron systems of the two functional groups (double bond and carbonyl group) are conjugated (the π-orbitals overlap in space). All the double bond π orbitals overlap. The C=C is polarised, with net 6? + on the terminal carbon.

Figure 10:
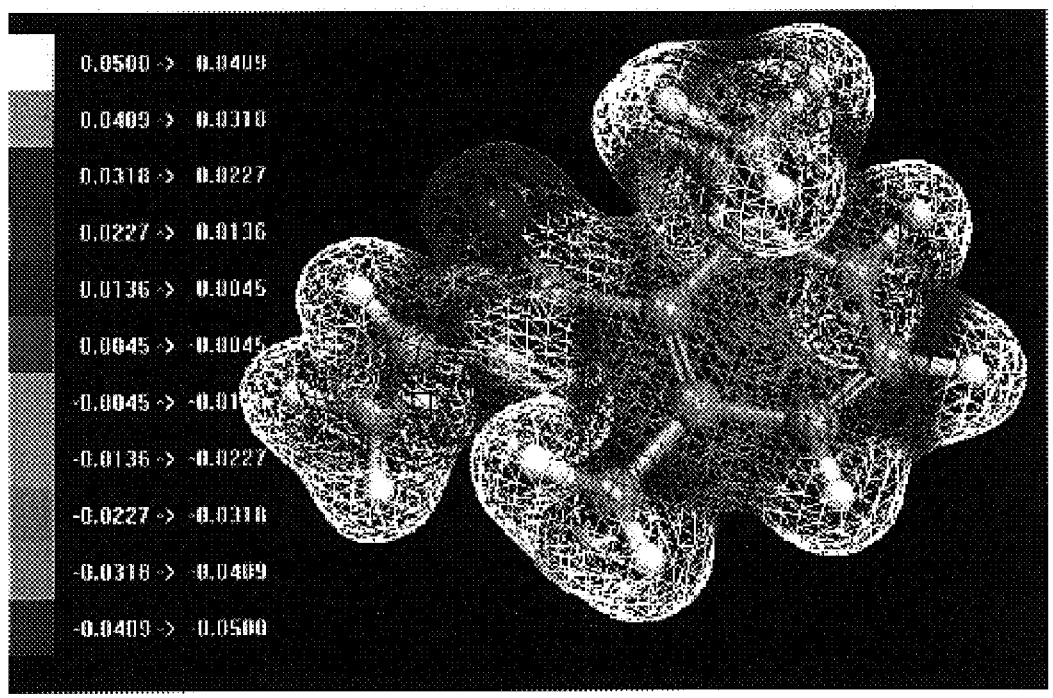
FIG. 10 is an ESP map of damascenone.

Some examples of these odorants are: 3R-(3α,3aβ,7β,8aα)]-1-(2,3,4,7,8,8a-Hexahydro-3,6,8,8-tetramethyl-1H-3a,7-methanoazulen-5-yl)ethan-1-one (vertofix), 1-(2,6,6-Trimethylcyclohexa-1,3-dienyl)-2-buten-1-one (damascenone) along with others present in other chemical classes discussed in this section, more notably in the ionone class. As an example damascenone's dipole moment calculation is shown below along with its ESP map in FIG. 10.

| Damascenone dipole moment |
|---|
| Dipole moment (Modified Del Re):
x component: 0.2889899
y component: 0.4444181
z component: 0.1702604
Total = 2.672575 debyes
= 8.91571018981934 × 10^−30 C m | hydrogen bond acceptor = 0.2773404
hydrogen bond donor = 1.043115E−02

Figure 11:
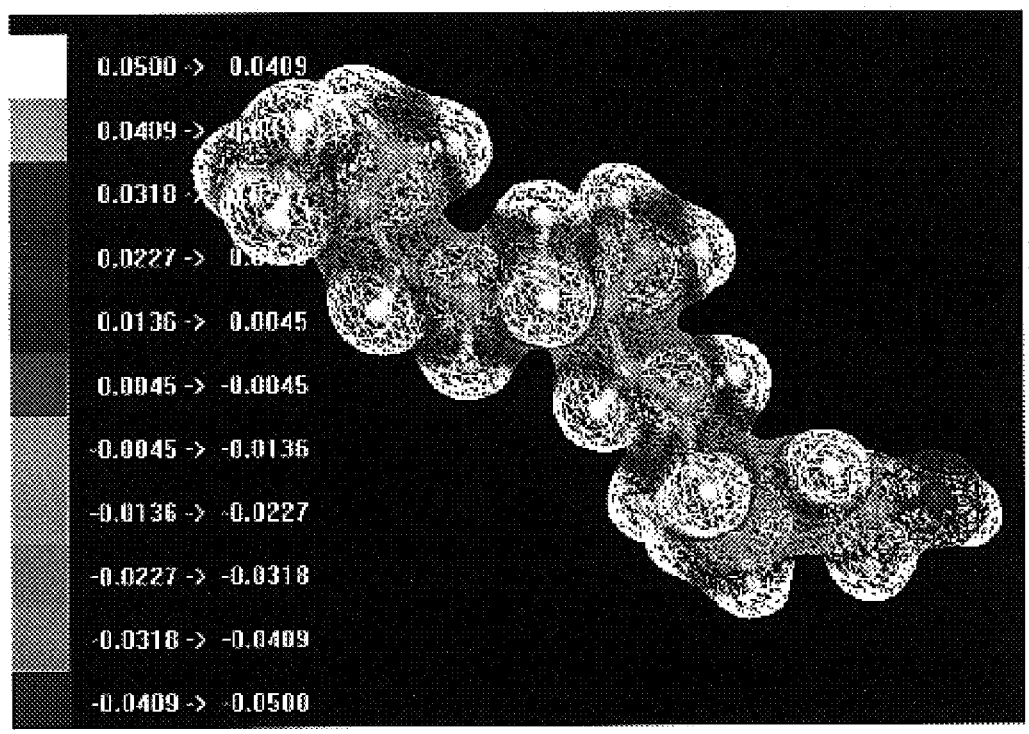
FIG. 11 is an ESP map of farnesol.

Odorants belonging to the chemical class referred to as □-enols will have a hydroxyl group adjacent to a double bond and will also exhibit strong dipole moment character. Some examples are trimethyl dodecatrienol; 3,7,11-Trimethyl-2,6,10-dodecatrien-1-ol (farnesol), 3,7,11-Trimethyidodeca-1,6,10-trien-3-ol (nerolidol). The hydrogen bonding calculation of farnesol along with its hydrogen bonding acceptor and donor index are shown below. The ESP map of farnesol is shown in FIG. 11.

| Farnesol dipole moment |
|---|
| Dipole moment (Modified Del Re):
x component: −0.1635251
y component: −0.5231593
z component: −2.493653E−02
Total = 2.6337 debyes
= 8.78602205085754 × 10^−30 C m | hydrogen bond acceptor = 0.4933752
hydrogen bond donor = 0.2640331

Figure 12:
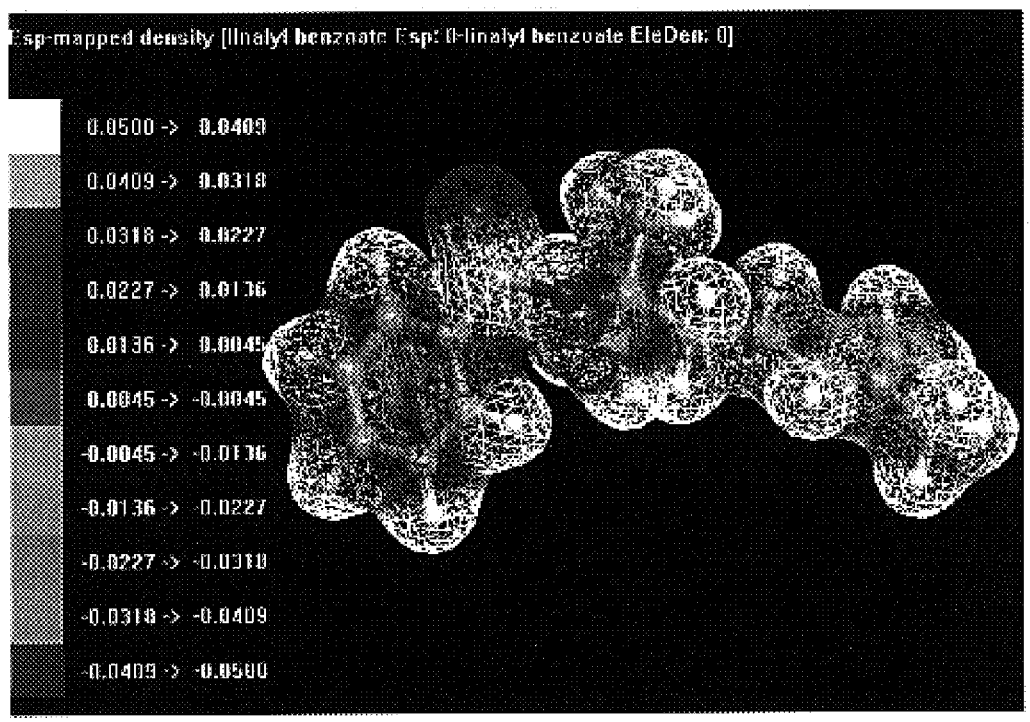
FIG. 12 is ESP map of linalyl benzoate.

Other odorants thought to work well against ammonia and other substituted amines are the high molecular weight aromatic esters such as the cinnamates, and the benzoates. Some of the examples are 3,7-dimethyl-1,6-octadien-3-yl benzoate (linalyl benzoate), 3,7-dimethyl-1,6-octadien-3-yl 3-phenyl-2-propenoate (linalyl cinnamate). The dipole moment calculation results for linalyl benzoate are shown below. The ESP map for linalyl benzoate is shown in FIG. 12.

| Linalyl benzoate dipole moment |
|---|
| Total Del Re charge = 5.960464E−08
Total PEOE charge = −1.282042E−07
Dipole moment (Modified Del Re):
x component: 0.3762744
y component: 1.449811E−02
z component: −6.869203E−02
Total = 1.837286 debyes
= 6.12918488788605 × 10^−30 C m | hydrogen bond acceptor = 0.4397368
hydrogen bond donor = 4.414128E−02

Figure 13:
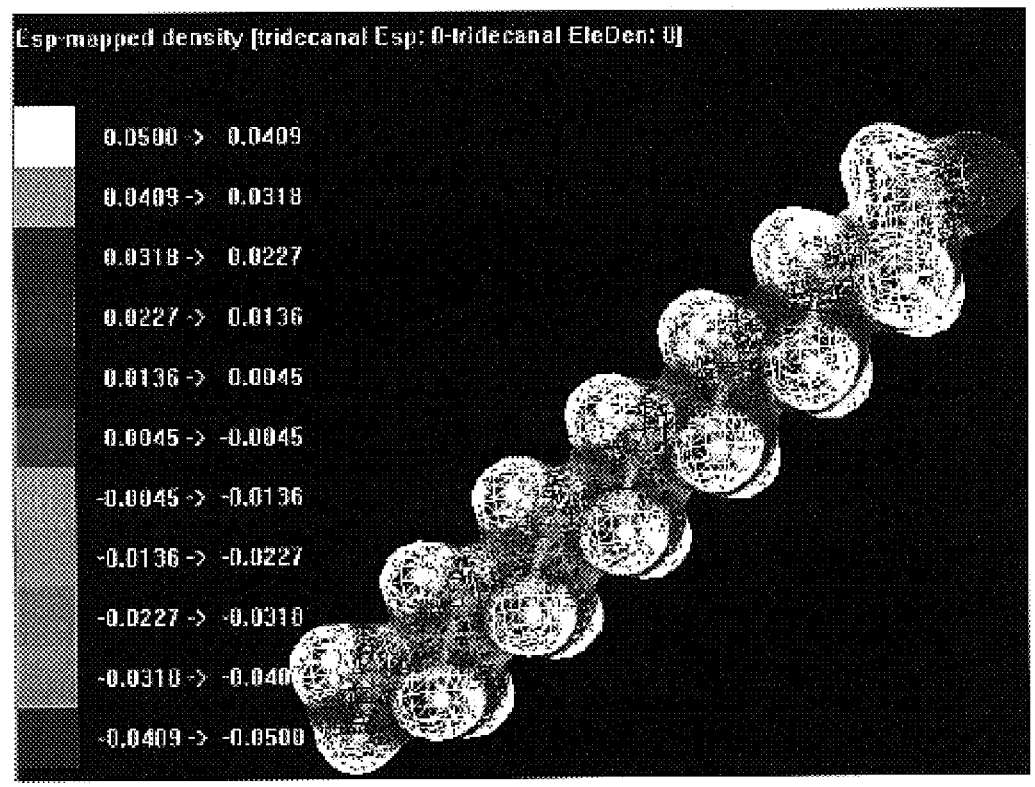
FIG. 13 is an ESP map of tridecanal.

Other odorants claimed in this invention belong to the saturated aldehydes functional group. They are for example 2-Methylundecanal, undecanal, 2-methyldecanal, tridecanal and will exhibit a very strong dipole moment. The dipole moment for tridecanal is shown below. The ESP map for tridecanal is shown in FIG. 13.

| Tridecanal dipole moment |
|---|
| Dipole moment (Modified Del Re):
x component: −0.5711196
y component: −0.181712
z component: 3.148407E−03
Total = 2.876825 debyes
= 9.59708930969238 × 10^−30 C m | hydrogen bond acceptor = 0.1791156
hydrogen bond donor = 1.733313E−02

Figure 14:
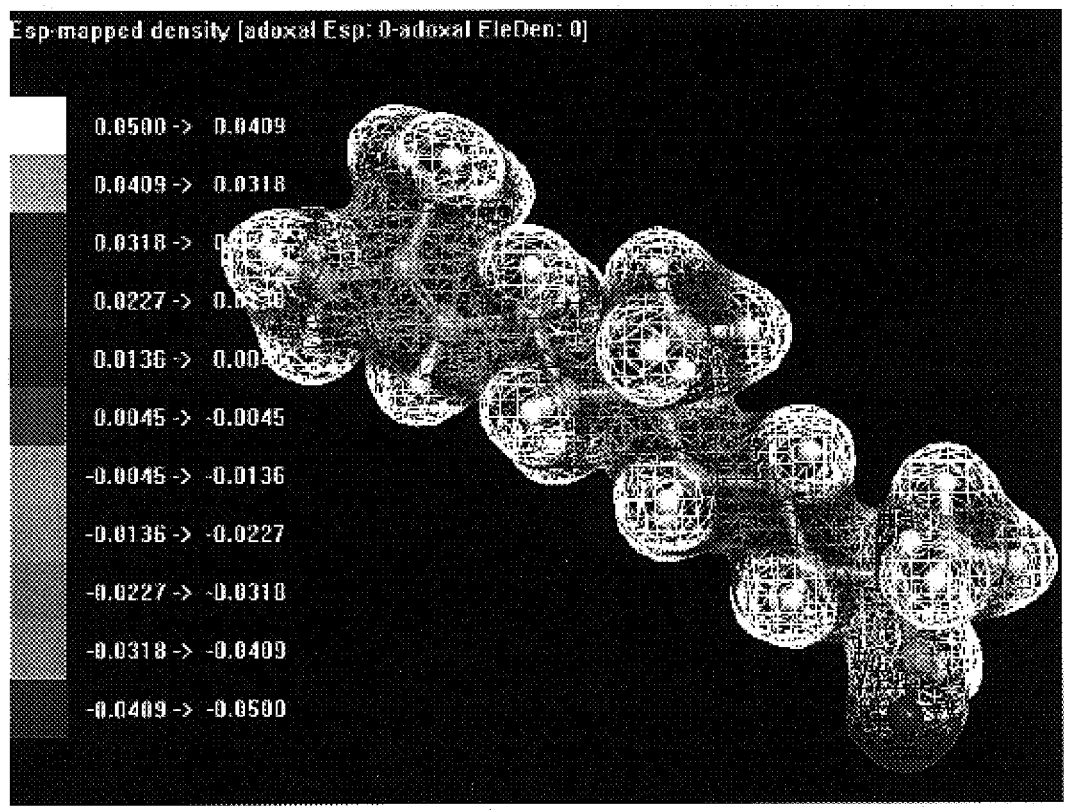
FIG. 14 is an ESP map for adoxal.

Odorant belong to the high molecular weight unsaturated aldehydes such as 2-methyl-4-(2,6,6-trimethylcyclohex-1-en-1-yl)-2-butenal (boronal), 2,6,10-trimethyl-9-undecenal; trimethyl undecylenic aldehyde (adoxal) also exhibit good ammonia and substituted amine malodor coverage properties. The dipole moment for adoxal is shown below and its ESP map in FIG. 14.

| Adoxal dipole moment |
| --- |
| Dipole moment (Modified Del Re):<br>   x component: −0.3561525<br>   y component: 0.4283556<br>   z component: −0.2738011<br>   Total = 2.979482 debyes<br>         = 9.93955332756043 × $10^{-30}$ C m | hydrogen bond acceptor = 0.2230104
hydrogen bond donor = 1.709307E−02

Figure 15:
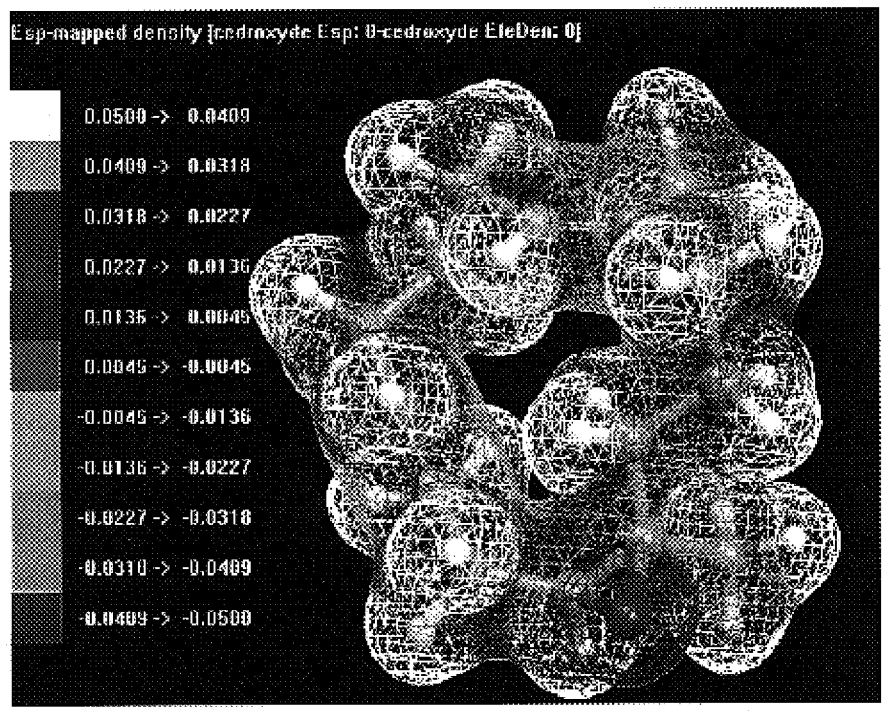
FIG. 15 is an ESP map for cedroxyde.

High clogP epoxides and ethers such as alpha cedrene epoxide, Isolongifolene epoxide, and cedroxide also exhibit dipole moments. The dipole moment for cedroxyde is shown below and its ESP map in FIG. 15.

| Cedroxyde dipole moment |
| --- |
| Dipole moment (Modified Del Re):<br>   x component: −0.299282<br>   y component: 0.2416269<br>   z component: −0.2051103<br>   Total = 2.092401 debyes<br>         = 6.98024982833862 × $10^{-30}$ C m | hydrogen bond acceptor = 0.2183856
hydrogen bond donor =

Figure 16:
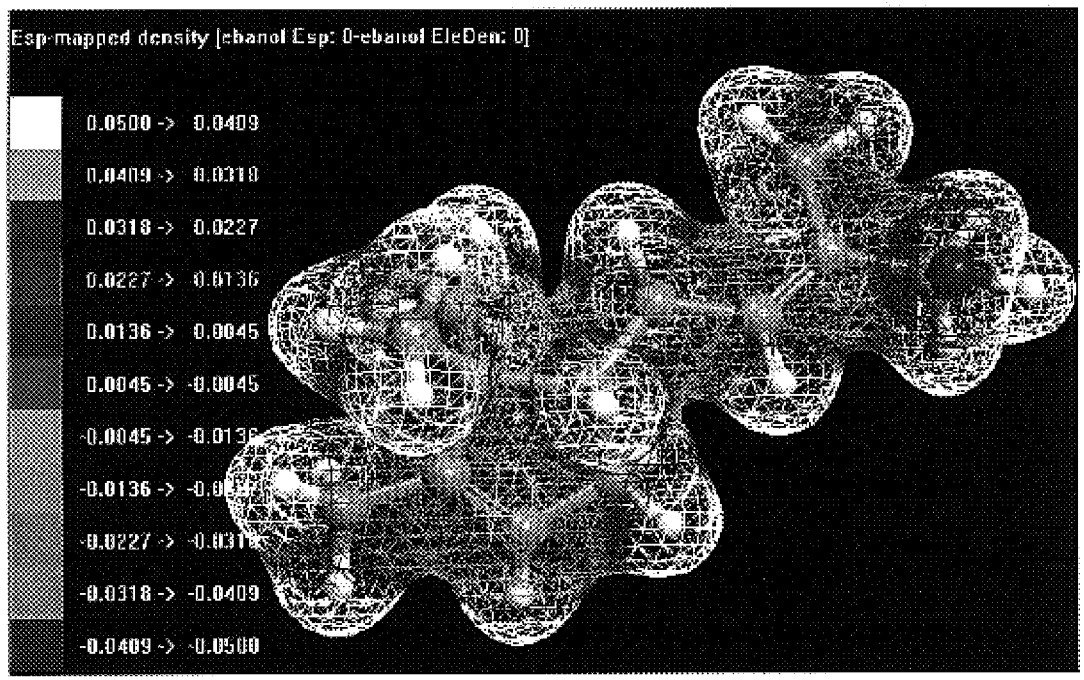
FIG. 16 is an ESP map of ebanol.

Odorants belonging to the sandalwood group are also very good ammonia and substituted amine malodor covering agents. Some of the examples are sandalore, bacdanol, ebanol, brahmanol. The dipole moment calculation results for ebanol are shown below and its ESP map is illustrated in FIG. 16.

| Ebanol dipole moment |
| --- |
| Dipole moment (Modified Del Re):<br>   x component: 0.3146157<br>   y component: −0.069792<br>   z component: −5.768216E−02<br>   Total = 1.57145 debyes<br>         = 5.24235718345642 × $10^{-30}$ C m | hydrogen bond acceptor = 0.4800614
hydrogen bond donor = 0.2625065

Figure 17:
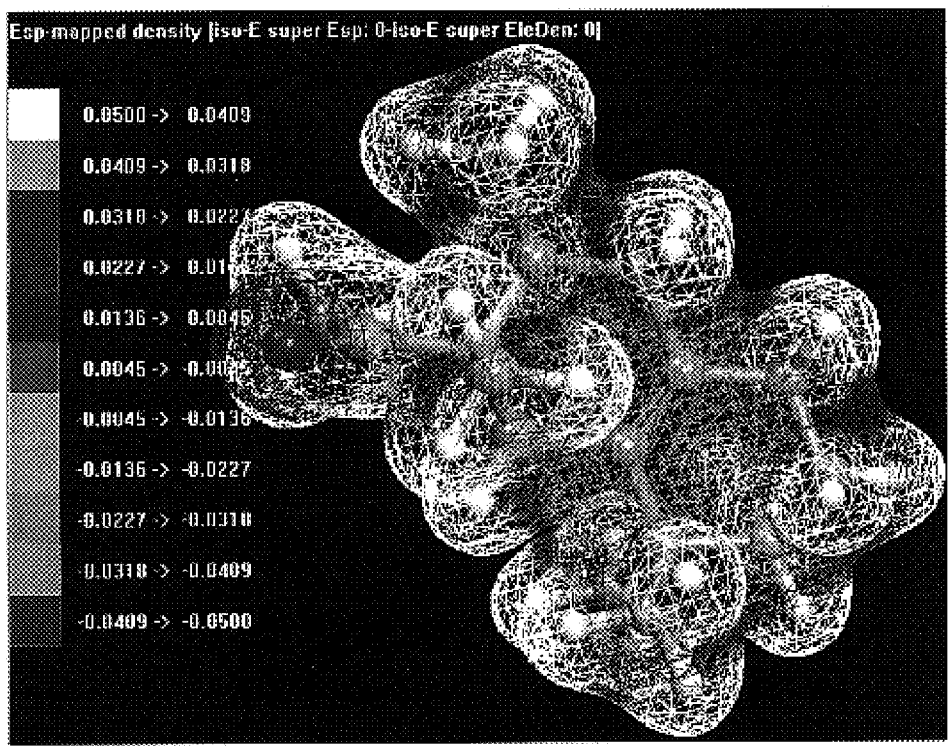
FIG. 17 shows an ESP map of iso-E super

Odorants with high clogP value and belonging to the unsaturated ketones are also part of this invention. The dipole moment for compound 1-(1,2,3,4,5,6,7,8-Octahydro-2,3,8,8-tetramethyl-2-naphthyl)ethan-1-one (iso-E super) is shown below along with an illustration of its ESP map in FIG. 17.

| Iso-E-super dipole moment |
| --- |
| Dipole moment (Modified Del Re):<br>   x component: 0.1300996<br>   y component: −0.1406988<br>   z component: −0.615339<br>   Total = 3.09354 debyes<br>         = 10.3200500793457 × $10^{-30}$ C m | hydrogen bond acceptor = 0.1995292
hydrogen bond donor =

Figure 18:
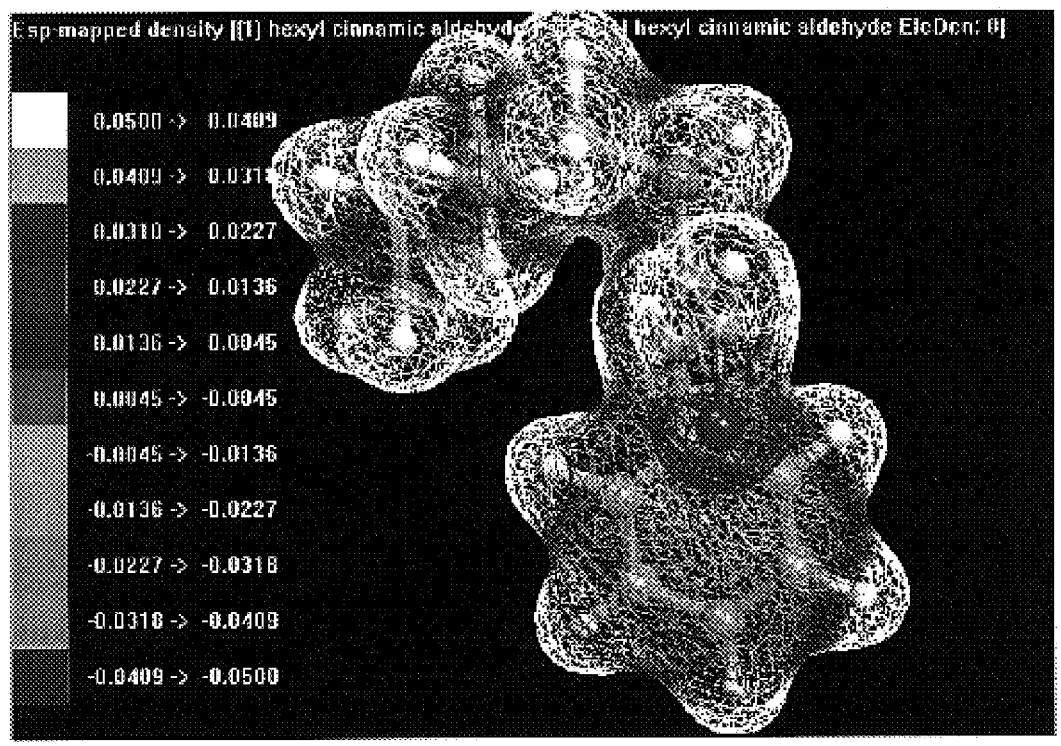
FIG. 18 is an ESP map of hexyl cinnamic aldehyde.

Hexyl cinnamic aldehyde and other odorants with high clogP value belonging to the cinnamic aldehydes group exhibit good ammonia and substituted amines coverage property. The dipole moment for hexyl cinnamic aldehyde is as follows below and its ESP map is shown in FIG. 18.

| Hexyl cinnamic aldehyde dipole moment |
| --- |
| Dipole moment (Modified Del Re):<br>   x component: −0.2997829<br>   y component: 0.6513566<br>   z component: −4.274428E−03<br>   Total = 3.441816 debyes<br>         = 11.4818976860046 × $10^{-30}$ C m | hydrogen bond acceptor = 0.2176229
hydrogen bond donor = 5.593472E−02

Figure 19:
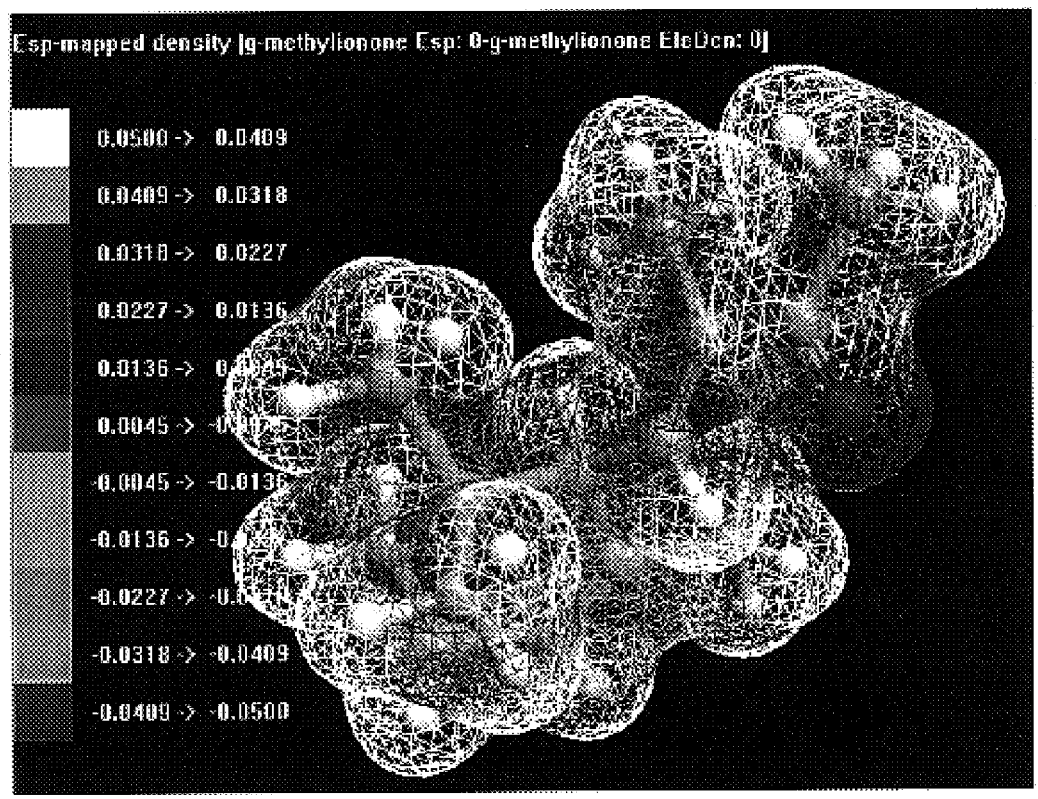
FIG. 19 is an ESP map of γ-methylionone.

Ionones are particularly efficacious in their ability to cover ammonia and amine malodor due to their strong dipole moment as discussed earlier added to low odor detection threshold values. Examples of this class of odorants are β-damascone, γ-methylionone, dynascone, α-ionone, β-ionone, etc. The dipole moment calculation for γ-methylionone is shown below and its ESP map in FIG. 19.

| γ-methylionone dipole moment |
| --- |
| Dipole moment (Modified Del Re):<br>   x component: −0.5023554<br>   y component: 0.2374173<br>   z component: −0.5562911<br>   Total = 3.773996 debyes<br>         = 12.5900502433777 × $10^{-30}$ C m | hydrogen bond acceptor = 0.2965091
hydrogen bond donor = 6.650686E−04

It is also important to establish that all potential perfumes for ammonia and other amine based hair color formulations must always be subjected to stability testing since predicting actual bond formation based on modeling (for example HOMO and LUMO orbital eigenvalues etc) is only an approximation. Stability issue and more specifically actual bond formation between these odorants and more likely substituted amines will depend on the concentration of the odorants, the level of amines present, the type of emulsion (CMC value), the amount of water, etc. and will differ from one formulation to another.

As an example, a stability study done for permanent hair color crème using a specific dye less base formulation by Jos H. Lowenstein and Sons Inc. (420 Morgan Avenue, Brooklyn, N.Y. 11222 USA) (10% ammonia hydroxide) is shown below for some odorants. Odorants were put up at 0.2% in the formulation, and odorants were subjected to 6 week stability testing at room temperature (R.T.) and 400C oven temperature. The odorants' performance was evaluated on a 5 point scale (E=excellent, VG=very good; G=good, F=fair; P=poor). Part of the results for some odorants and for the first 4 weeks is shown below. This example is important in establishing the importance of subjecting every perfume to stability testing, upon identifying good ammonia and substituted amine malodor covering compounds.

TABLE 7

| Raw Material | 1 Week | | 2 Weeks | | 3 Weeks | | 4 Weeks | |
| --- | --- | --- | --- | --- | --- | --- | --- | --- |
| | RT | Oven | RT | Oven | RT | Oven | RT | Oven |
| MUSCENONE @ 10% DPG | F | F | F | F | F | F | F | F |
| FLOROL | F | F | P | P | P | P | P | P |
| ORANGE ALDEHYDE 500 | VG | G | G | G | G | F | G | F |
| ALLYL AMYL GLYCOLATE | G | G | G | F | G | F | G | F |
| FLORALOZONE | G | G | G | G | G | G | G | G |
| BETA DAMASCONE | E | VG | E | VG | VG | G | VG | G |
| BENZYL SALICYLATE | G | G | G | G | F | F | F | F |
| CIS-3-HEXENYL ACETATE @ 10% DPG | G | G | G | G | F | F | F | F |
| ETHYL ACETOACETATE (discolors in oven) | F | F | F | F | F | F | F | F |
| HEXYL CINNAMIC ALDEHYDE (cloudy) | G | G | G | G | G | G | G | G |
| TRANS-2-HEXENAL @ 10% DPG | G | F | G | F | G | F | F | F |
| CIS-3-HEXENOL @ 10% DPG | VG | G | VG | G | G | G | G | G |
| LILIAL | G | G | G | G | G | G | G | G |
| LINALOOL SYNTHETIC | G | G | G | G | G | G | G | G |
| ORANGE TERPENES | G | F | G | F | G | F | G | F |

C. Illustrative Perfume Examples

As an illustration, perfumes were constructed using odorants with high flux and air impact values as well as odorants with the ability to complex the lone pair of electrons on the N atom present in ammonia and other substituted amines, as described previously in the herein invention.

These perfumes will contain at least one high flux ($\alpha$) and air impact odorant ($\phi$) in addition to an odorant able to mask ammonia based on its high dipole moment value. Odorants with $\alpha^*\phi$ are shown in bold and odorants with dipole moments of at least 1.5 debye are in italic (see below perfume examples).

The first perfume used in this section is a fruity-floral type. (See Example 1.) This fragrance was put at 1% in a hair color permanent crème provided by Jos. H. Lowenstein and upon evaluating found to have excellent covering properties in addition to being stable.

Example 1

Fruity—Floral Perfume

| | parts |
| --- | --- |
| ALLYL CAPROATE | 1.0 |
| AMYL CINNAMIC ALDEHYDE | 1.9 |
| BENZYL ACETATE | 7.5 |
| BENZYL SALICYLATE | 12.1 |
| CIS-3-HEXEN-1-OL | 0.1 |
| CYCLACET | 4.5 |
| d-LIMONENE | 5.0 |
| DYNASCONE 10% DPG | 0.7 |
| ETHYL 2-METHYLBUTYRATE PURE FCC | 3.0 |
| ETHYLENE BRASSYLATE | 5.3 |
| FLOROL | 0.5 |
| FRUCTONE | 1.5 |
| GALAXOLIDE 50 DEP | 13.7 |
| GAMMA UNDECALACTONE | 2.5 |
| GERANIOL | 1.3 |
| HEDIONE | 5.8 |
| HEXYL ACETATE | 0.9 |
| HEXYL CINNAMIC ALDEHYDE | 3.0 |
| IONONE ALPHA REGULAR | 2.6 |
| IONONE BETA | 0.7 |
| ISO E SUPER | 1.2 |
| LIFFAROME | 1.7 |
| LILIAL | 3.2 |

-continued

| | parts |
| --- | --- |
| LINALOOL | 4.5 |
| LINALYL ACETATE | 1.5 |
| LYRAL | 1.0 |
| MANZANATE | 1.5 |
| MAYOL | 0.9 |
| METHYL IONONE GAMMA A | 1.8 |
| METHYL PHENYL CARBINYL ACETATE | 0.7 |
| PHENYL ETHYL ACETATE | 0.2 |
| PHENYL ETHYL ALCOHOL | 2.2 |
| ROMASCONE | 0.5 |
| TRICYCLODECENYL PROPIONATE | 0.5 |
| TRIPLAL | 0.5 |
| UNDECAVERTOL | 0.9 |
| VERDOX | 3.5 |
| | 100.0 |

The second example is a citrus floral perfume that provides excellent ammonia coverage and is stable in the same formulation as above in which it was put at 1%. (See Example 2.)

Example 2

Citrus—Floral Perfume

| ODORANTS | PARTS |
| --- | --- |
| ALPHA TERPINEOL | 3.5 |
| alpha-DAMASCONE | 0.5 |
| BACDANOL | 2.5 |
| BENZYL ACETATE | 15 |
| BENZYL SALICYLATE | 2.5 |
| CIS-3-HEXENYL ACETATE | 0.1 |
| CITRONELLOL | 1.5 |
| FRUCTONE | 2 |
| DIHYDROMYRCENOL | 20 |
| DIMETHYL BENZYL CARBINYL ACETATE | 1.5 |
| d-LIMONENE | 22 |
| ETHYL 2-METHYLBUTYRATE | 0.4 |
| GALAXOLIDE 50 DEP | 4.4 |
| GAMMA UNDECALACTONE | 0.2 |
| GAMMA-DECALACTONE | 0.2 |
| GERANYL ACETATE | 1 |
| HEDIONE | 4.5 |
| HELIONAL | 2 |

-continued

| ODORANTS | PARTS |
|---|---|
| ISO E SUPER | 3 |
| ISOAMYL ISOVALERATE | 0.2 |
| MANZANATE | 0.4 |
| AMYL VINYL CARBINOL | 1.5 |
| NOPYL ACETATE | 2.5 |
| PATCHOULY OIL | 1.2 |
| PHENYL ETHYL ALCOHOL | 4.9 |
| ROSE OXIDE (HIGH CIS) | 0.5 |
| TRIPLAL | 0.5 |
| LIFFAROME | 1 |
| NEOPROXEN | 0.5 |
| | 100 |

The "woody-musk perfume" provided in Example 3 has very good ammonia coverage when put at 1% in the permanent dye less crème described above as well.

Example 3

Woody—Musk Perfume

| | parts |
|---|---|
| AMBROXAN | 17 |
| ETHYLENE BRASSYLATE | 18 |
| ISO E SUPER | 11 |
| BETA DAMASCONE FAB | 3 |
| CASHMERAN | 2 |
| MANZANATE | 7 |
| VERDOX | 2 |
| HEDIONE HC | 5 |
| EBANOL | 6 |
| GALAXOLIDE DPG 50% | 28 |
| LIFFAROME | 1 |
| | 100 |

What is claimed is:

1. A method of formulating a fragrance to reduce malodor in a nitrogen-based product, comprising:
    calculating air impact values for a group of odorants;
    calculating flux values for the group of odorants;
    calculating the product of the flux value and the air impact value;
    selecting at least a first odorant having the product of air impact and flux value equaling about $5 \times 10^{-13}$ or greater to form the fragrance; and
    adding the selected odorant to the product to mask the nitrogen-based malodor.

2. The method of claim 1, additionally comprising the steps of:
    calculating odor detection thresholds for the group of odorants; and
    selecting the odorant having an odor detection threshold of about 50 ppb and less in addition to having a product of air impact and flux value of about $5 \times 10^{-13}$ or greater.

3. The method of claim 1, further comprising the steps of:
    calculating dipole moments for the group of odorants;
    calculating clogP values for the group of odorants;
    calculating hydrogen bond donor and hydrogen bond acceptor indexes for the group of odorants;
    selecting at least a second malodor-reducing odorant having a dipole moment of about 1.7 debye and greater, a clogP value of about 4.0 or greater and either a hydrogen bond donor or a hydrogen bond acceptor index of at least about 0.1 or greater; and
    adding the second odorant to the first odorant to form the fragrance.

4. The method of claim 1, wherein the product is an emulsion having a ratio of 20% oil to 80% water.

5. The method of claim 1, wherein the nitrogen-based component is selected from the group consisting of ammonia, a substituted amine, and combinations of these.

6. The method of claim 1, wherein the product is a hair coloring product.

7. The method of claim 1, wherein the fragrance comprises 1% by weight of the product.

8. A method of formulating a fragrance to reduce malodor in a nitrogen-based product, comprising:
    calculating dipole moments for a group of odorants;
    calculating clogP values for the group of odorants;
    calculating hydrogen bond donor and hydrogen bond acceptor indexes for the group of odorants; and
    selecting at least a first odorant having a dipole moment of about 1.7 debye or greater, a clogP value of about 4.0 or greater, and either a hydrogen bond donor or a hydrogen bond acceptor index of about 0.1 or greater to form the fragrance;
    adding the selected odorant to the product to mask the nitrogen-based malodor.

9. The method of claim 8, additionally comprising the steps of:
    calculating air impact values for a group of odorants;
    calculating flux value values for the group of odorants, the flux value calculation based upon the product having ant oil to water ratio of 20% oil to about 80% water;
    calculating the product of the flux values and the air impact values for the group of odorants;
    selecting at least a second odorant having the product of air impact and flux value equaling about $5 \times 10^{-13}$ or greater; and
    adding the selected odorant to the fragrance.

10. The method of claim 9, further comprising the steps of:
    calculating the odor detection threshold of the group of odorants;
    selecting the second odorant having an odor detection threshold less than about 50 ppb in addition to having a product of air impact and flux value of $5 \times 10^{-13}$ or greater.

11. The method of claim 8, wherein the nitrogen-based component is selected from the group consisting of ammonia, a substituted amine, and combinations of these.

12. The method of claim 8, wherein the product is a hair coloring product.

13. The method of claim 8, wherein the fragrance comprises about 1% by weight of the product.

* * * * *